(12) United States Patent
Dave et al.

(10) Patent No.: US 8,754,207 B2
(45) Date of Patent: Jun. 17, 2014

(54) PROCESS FOR THE PREPARATION OF RAPAMYCIN DERIVATIVES

(75) Inventors: Mayank Ghanshyambhai Dave, Gujarat (IN); Bipin Pandey, Gujarat (IN)

(73) Assignee: Cadila Healthcare Limited, Ahmedabad, Gujaret (IN)

( * ) Notice: Subject to any disclaimer, the term of this patent is extended or adjusted under 35 U.S.C. 154(b) by 150 days.

(21) Appl. No.: 13/497,416

(22) PCT Filed: Sep. 24, 2010

(86) PCT No.: PCT/IN2010/000646
§ 371 (c)(1),
(2), (4) Date: Apr. 25, 2012

(87) PCT Pub. No.: WO2011/051960
PCT Pub. Date: May 5, 2011

(65) Prior Publication Data
US 2012/0202988 A1 Aug. 9, 2012

(30) Foreign Application Priority Data
Sep. 25, 2009 (IN) .......................... 2234/MUM/2009

(51) Int. Cl.
C07D 498/18 (2006.01)
C07D 319/06 (2006.01)
C07D 319/08 (2006.01)

(52) U.S. Cl.
USPC .......................... 540/456; 549/330; 549/357

(58) Field of Classification Search
USPC ................................... 540/456; 549/330, 357
See application file for complete search history.

(56) References Cited

U.S. PATENT DOCUMENTS

| | | | |
|---|---|---|---|
| 5,362,718 | A | 11/1994 | Skotnicki et al. |
| 6,277,983 | B1 | 8/2001 | Shaw et al. |
| 2005/0234086 | A1 | 10/2005 | Gu et al. |
| 2007/0129395 | A1 | 6/2007 | Deshmukh et al. |

FOREIGN PATENT DOCUMENTS

| | | |
|---|---|---|
| WO | 03/099787 | 12/2003 |
| WO | WO 2005/016935 | 2/2005 |
| WO | WO 2005/035528 | 4/2005 |
| WO | WO 2006/095185 | 9/2006 |

OTHER PUBLICATIONS

International Search Report mailed Apr. 19, 2011.
Written Opinion of the International Searching Authority mailed Apr. 19, 2011.
L. Sorbera et al., "CCI-779: Oncolytic mTOR Inhibitor", Drugs of the Future 2002, Prous Science 2002, vol. 27, No. 1, 2002, Prous Science 2002, pp. 7-13.
G. Jianxin et al., "Lipase-Catalyzed Regioselective Esterification of Rapamycin: Synthesis of Temsirolimus (CCI-779)", Organic Letters, Sep. 1, 2005, vol. 7, No. 18, pp. 3945-3948.
C. Yanqiu et al., "Conformational Changes of Rapamycin and Analogs Upon Complexing with FKBP Associated with Activity: An Application of Second Derivative CD Spectroscopy", Journal of the American Chemical Society, vol. 116, No. 6, 1994, pp. 2683-2684.
Bruice et al. "A Search for Carboxyl-Group Catalysis in Ketal hydrolysis" *Journal of the American Chemical Society*, 89(14):3568-3576 (1967).

*Primary Examiner* — Bruck Kifle
(74) *Attorney, Agent, or Firm* — Nixon & Vanderhye P.C.

(57) ABSTRACT

The invention relates to processes for the preparation of compound of CCI-779 having the Formula (I), which is useful as an antineoplastic agent. The invention further relates to certain novel intermediates useful in the preparation of compound of CCI-779 and processes for their preparation. The invention also relates to pharmaceutical compositions that include the compound of CCI-779, prepared according to the processes disclosed herein.

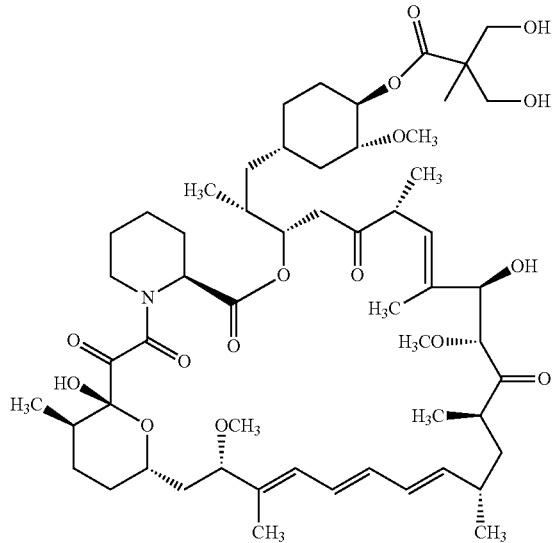

Formula (I) or CCI-779

25 Claims, 3 Drawing Sheets

PROCESS FOR THE PREPARATION OF RAPAMYCIN DERIVATIVES

This application is the U.S. national phase of International Application No. PCT/IN2010/000646 filed 24 Sep. 2010 which designated the U.S. and claims priority to IN 2234/MUM/2009 filed 25 Sep. 2009, the entire contents of each of which are hereby incorporated by reference.

FIELD OF THE INVENTION

The invention relates to processes for the preparation of CCI-779 having the Formula (I), which is useful as an antineoplastic agent. The invention further relates to certain novel intermediates useful in the preparation of CCI-779 and processes for their preparation. The invention also relates to pharmaceutical compositions that include the CCI-779, prepared according to the processes disclosed herein.

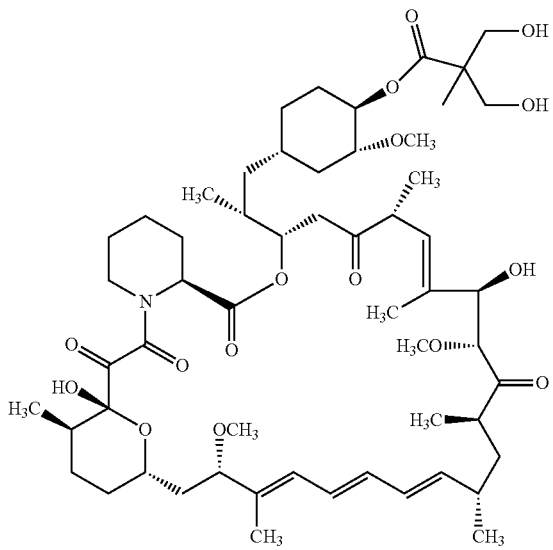

Formula (I) or CCI-779

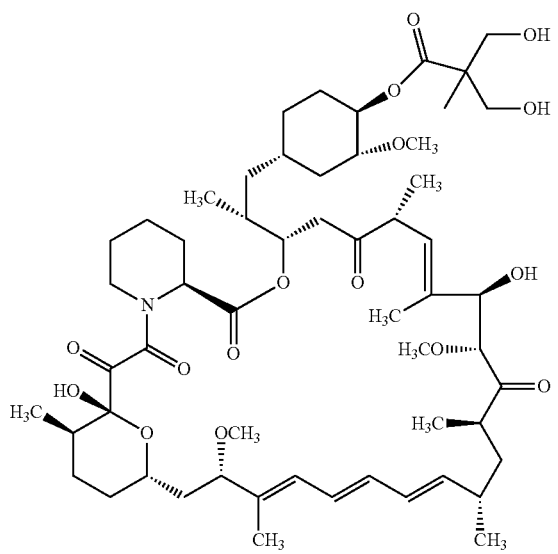

Formula (I) or CCI-779

BACKGROUND OF THE INVENTION

Rapamycin 42-ester of 3-hydroxy-2-(hydroxymethyl)-2-methylpropionic acid (CCI-779) is an ester of rapamycin, commercially known as Temsirolimus, which has demonstrated significant inhibitory effects on tumor growth both in vitro and in vivo models including humans. CCI-779 may delay the time to progression of tumors or time to tumor recurrence, which is more typical of cytostatic rather than cytotoxic agents. CCI-779 is considered to have a mechanism of action that is similar to that of sirolimus.

The preparation and use of hydroxyesters of rapamycin, including CCI-779, are disclosed in U.S. Pat. No. 5,362,718. CCI-779 can be synthesized by the non-regioselective acylation of rapamycin, as described in Example 10 of the U.S. Pat. No. 5,362,718. The synthesis, however, is complicated due to the presence of mixtures of the desired 42-ester, with 31-esterified rapamycin, as well as 31, 42-diesterified rapamycin and unreacted rapamycin. In an effort to consume the remaining starting rapamycin, the reaction was allowed to proceed for a longer period with negative consequences, the quantity of the 31, 42-bisester increased significantly. The resulting crude product [I] is contaminated with unreacted rapamycin and 31, 42-bisester, and subsequent column chromatography purification effort has proved to be difficult because of a very close retention time with product [I]. Overall, the major obstacle in large-scale production of compound [I] as per the process of the above patent appears to be the non-regiospecificity that is further complicated by purification difficulties, due to similarity of functional groups.

CCI-779 can also be prepared by the acylation of the 31-silyl ether of rapamycin with a ketal of bis-(hydroxymethyl) propionic acid, followed by removal of the 31-silyl ether and ketal protecting group from the bis-(hydroxymethyl)propionic acid, as described in U.S. Pat. No. 6,277,983. However, the crude 42-monoester produced from this regioselective synthesis requires further purification by column chromatography to remove residual amounts of diester by-products and unreacted rapamycin starting material.

International (PCT) Publication No. WO 2005016935 discloses a process for the preparation of 42-ester of rapamycin using boronic acid chemistry. The process involves acylating a rapamycine 31-silyl ether; selective hydrolysis of the 42-ester boronate 31-silyl ether; and treating the rapamycine 42-ester boronate with a suitable diol.

U.S. Publication No. 2005234086 describes synthesis of CCI-779 using enzyme Lipase as a catalyst but there are several disadvantages of the use of enzymatic catalysis on an industrial scale, for instance in terms of volume, work-up and overall cost.

U.S. Publication No. 20070129395 describes synthesis of purified crystalline CCI-779. The specification also discloses purified crystalline CCI-779 having a DSC thermogram having an endotherm peak greater than about 165° C. and an XRD peak pattern having peaks at 2 theta of about 7.7, 9.0, 11.4, 12.6, 13.3, 15.0, 15.4, 16.2, 66.5, 34.8, 43.7, 31.4 and 58.

Several of the above processes either have a problem of low yield and purity or are difficult to carry out on a commercial scale and are expensive. Therefore, there is a need to provide a process for the preparation of a compound of Formula (I), which is regio-selective, cost effective, scalable, and industrially applicable. The present invention provides a process, which is efficient, cost effective and does not result in impure product, thus making the process amenable for commercial scale use.

SUMMARY OF THE INVENTION

In one general aspect there is provided a process for the preparation of CCI-779.

The process includes:

i) reacting rapamycin of Formula (R),

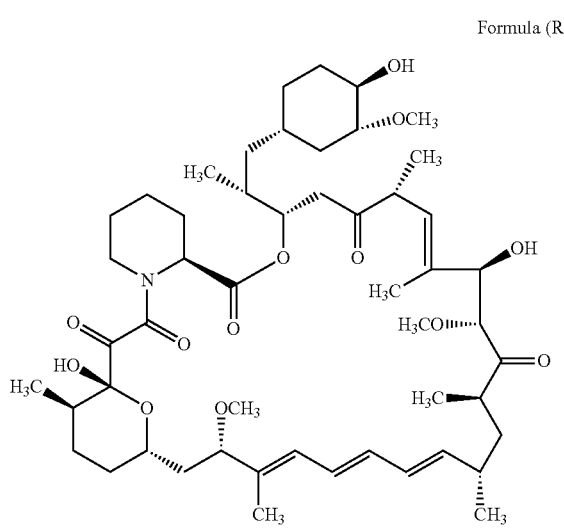

Formula (R)

with one or more suitable acylating agents in the presence of one or more suitable bases to give a compound of Formula (Ia);

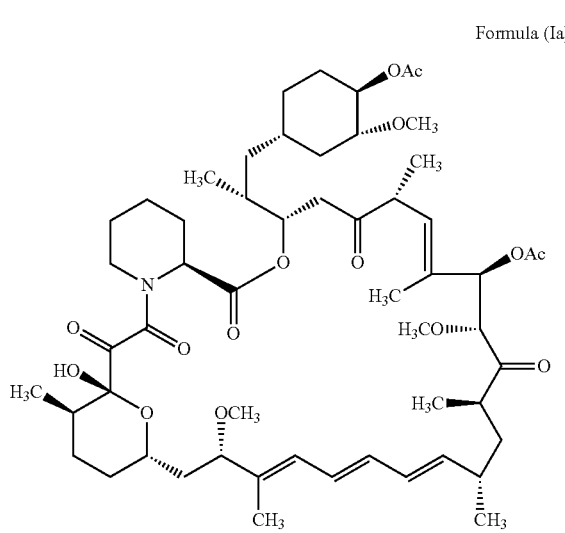

Formula (Ia)

(ii) converting the compound of Formula (Ia) to 31-monoacetate of

Formula (Ib) by using one or more suitable bases in one or more suitable solvents;

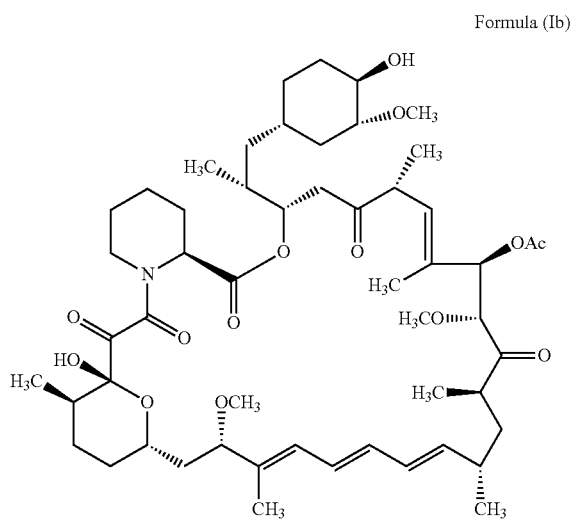

Formula (Ib)

(iii) selectively esterifying the 31-monoacetate of rapamycin of the compound of Formula (Ib) at 42-position to obtain a compound of Formula (Ic) with a suitable esterification reagent in one or more suitable solvents; and

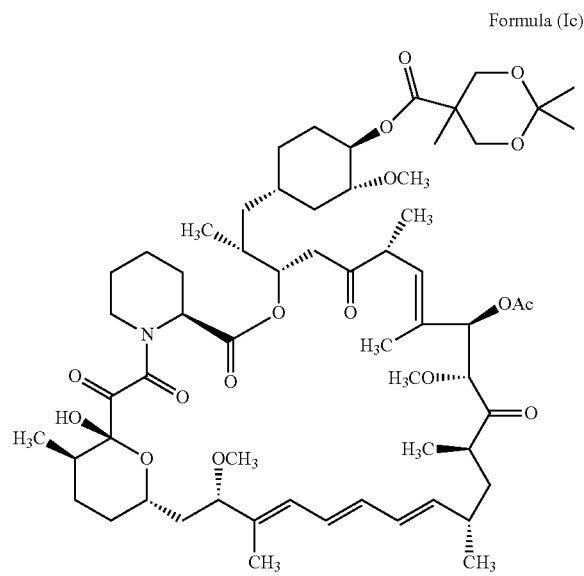

Formula (Ic)

iv) deprotecting the 42-ester and 31-acetyl group of the compound of Formula (Ic) with one or more suitable acid in one or more suitable solvents to give the CCI-779 of Formula (I).

In another general aspect there is provided a process for the preparation of CCI-779 of Formula (I). The process includes:
(i) reacting 2,2-bis(hydroxymethyl)propionic acid of formula (A), Formula (A)

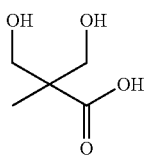

with a suitable ketal of Formula (IIa) in the presence of a suitable acid catalyst to obtain a compound of Formula (IIb), Formula (IIa)

Formula (IIb)

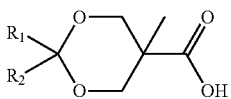

wherein, 'R' is selected from lower alkyl groups; and $R_1$ and $R_2$ independently represents $C_1$ to $C_{10}$ alkyl, $C_5$ to $C_{10}$ aryl groups, or $R_1$ and $R_2$ together with the carbon atom to which they are attached forms a $C_4$-$C_{10}$ cyclic ring, optionally substituted with one or more groups selected from halogens, hydroxy ($C_1$-$C_4$)alkyl, ($C_1$-$C_4$)alkoxy, or haloalkyl groups, or bicyclic rings which may further be optionally substituted with one or more groups selected from halogens, hydroxy, ($C_1$-$C_4$)alkyl, ($C_1$-$C_4$)alkoxy, or haloalkyl groups, or tricyclic ring optionally substituted with one or more groups selected from halogens, hydroxy, ($C_1$-$C_4$)alkyl, ($C_1$-$C_4$)alkoxy, or haloalkyl groups; Examples of suitable bicyclic groups as substituents on either $R_1$ or $R_2$ includes camphor, substituted camphor and the like. Examples of suitable tricyclic groups as substituents on either $R_1$ or $R_2$ includes fluorenone and substituted fluorenone and the like.
(ii) reacting the compound of Formula (IIb) with one or more suitable acylating agents in the presence of one or more suitable bases to form a mixed anhydride of a compound of Formula (IIc), wherein $R_1$ and $R_2$ are as defined above;

Formula (IIc)

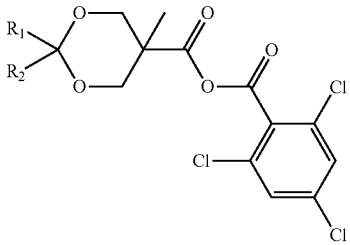

(iii) reacting the compound of Formula (IIc) with rapamycin or 31-protected rapamycin in the presence of one or more suitable bases to give a suitably protected 42-ester of rapamycin (IId), wherein $R_1$ and $R_2$ are as defined above and 'P' is either H or a suitable protecting group; and Formula (IId)

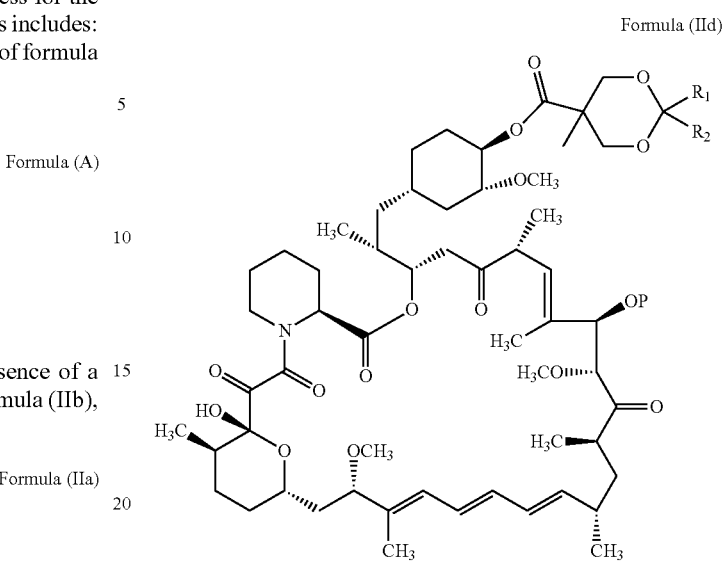

(iv) hydrolyzing the compound of Formula (IId) with a suitable acid to obtain the CCI-779 of the compound of Formula (I).

In another general aspect there is provided a compound of Formula (IIb), (IIc) and (IId) and their use for the preparation of CCI-779 of Formula (I).

Formula (IIb)

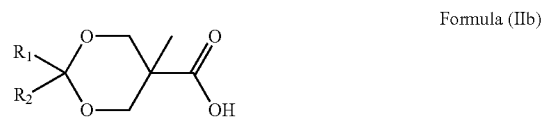

Formula (IIc)

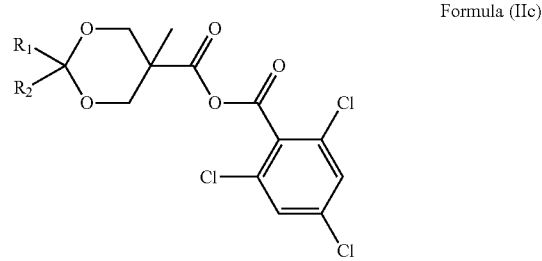

Formula (IId)

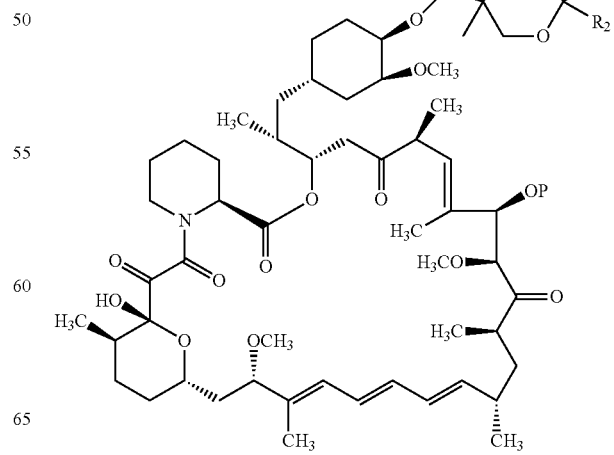

'R' is selected from lower alkyl groups; $R_1$ and $R_2$ independently represents $C_1$ to $C_{10}$ alkyl, $C_5$ to $C_{10}$ aryl groups or $R_1$ and $R_2$ together with the carbon atom to which they are attached forms a $C_4$-$C_{10}$ cyclic ring, optionally substituted with one or more groups selected from halogens; hydroxy; $(C_1$-$C_4)$alkyl; $(C_1$-$C_4)$alkoxy; or haloalkyl groups or bicyclic rings which may further be optionally substituted with one or more groups selected from halogens, hydroxy, $(C_1$-$C_4)$alkyl, $(C_1$-$C_4)$alkoxy, or haloalkyl groups; or tricyclic ring optionally substituted with one or more groups selected from halogens, hydroxy, $(C_1$-$C_4)$alkyl, $(C_1$-$C_4)$alkoxy, or haloalkyl groups. Examples of suitable bicyclic groups as substituents on either $R_1$ or $R_2$ includes camphor, substituted camphor and the like. Examples of suitable tricyclic groups as substituents on either $R_1$ or $R_2$ includes fluorenone and substituted fluorenone and the like. 'P' is either H or a suitable protecting group.

In another general aspect there is provided a compound of Formula (Ia) and their use for the preparation of CCI-779 of Formula (I).

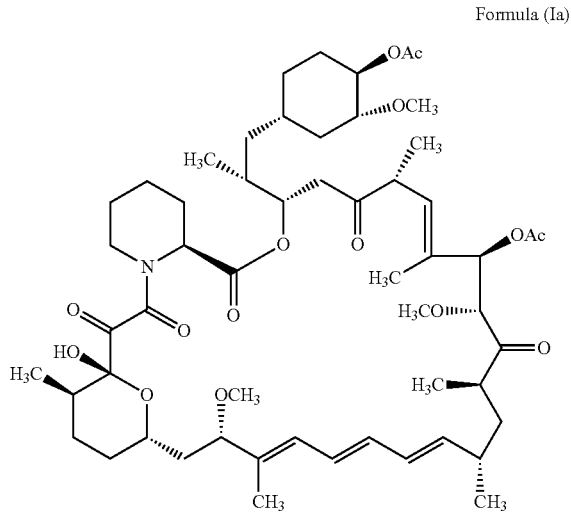 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(C)=O)[C@H](OC)C2)CC(=O)[C@H](C)/C=C(\C)[C@@H](OC(C)=O)[C@@H](OC)C(=O)[C@H](C)C[C@H](C)/C=C/C=C/C=C/1C]

Formula (Ia)

The product so obtained may be further or additionally purified by Preparative HPLC to obtain desired purity levels.

The process may include further forming the product so obtained into a finished dosage form.

The details of one or more embodiments of the invention are set forth in the description below. Other features, objects and advantages of the invention will be apparent from the description and claims.

DETAILED DESCRIPTION OF THE INVENTION

Figure 1:
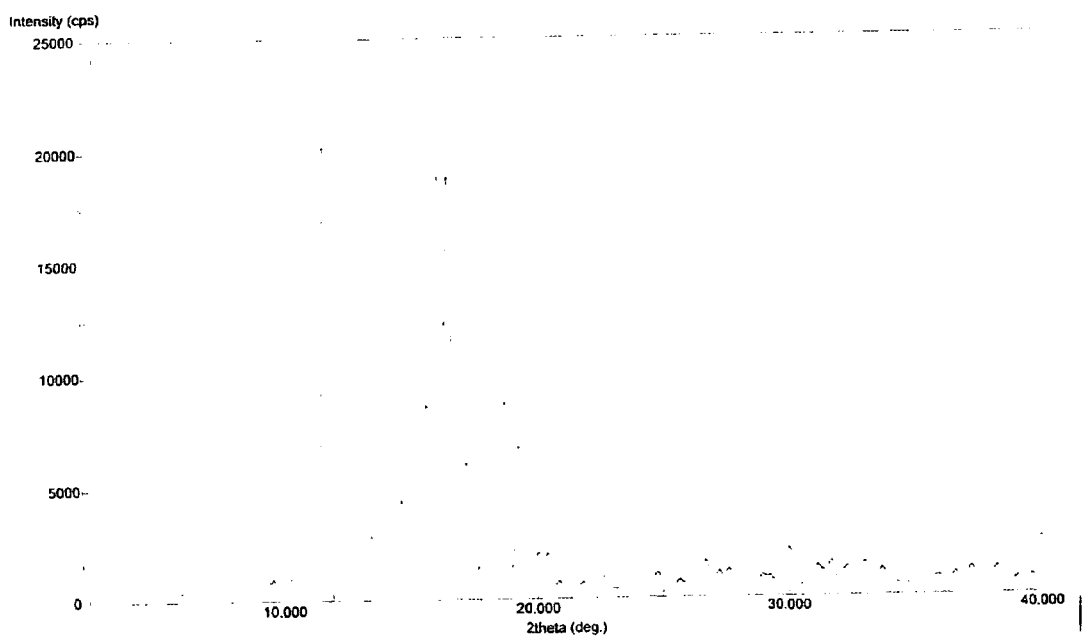
FIG. 1 is a powder X-ray diffraction (XRPD) pattern of compound of Formula (IIb1) according to the present invention.
Figure 2:
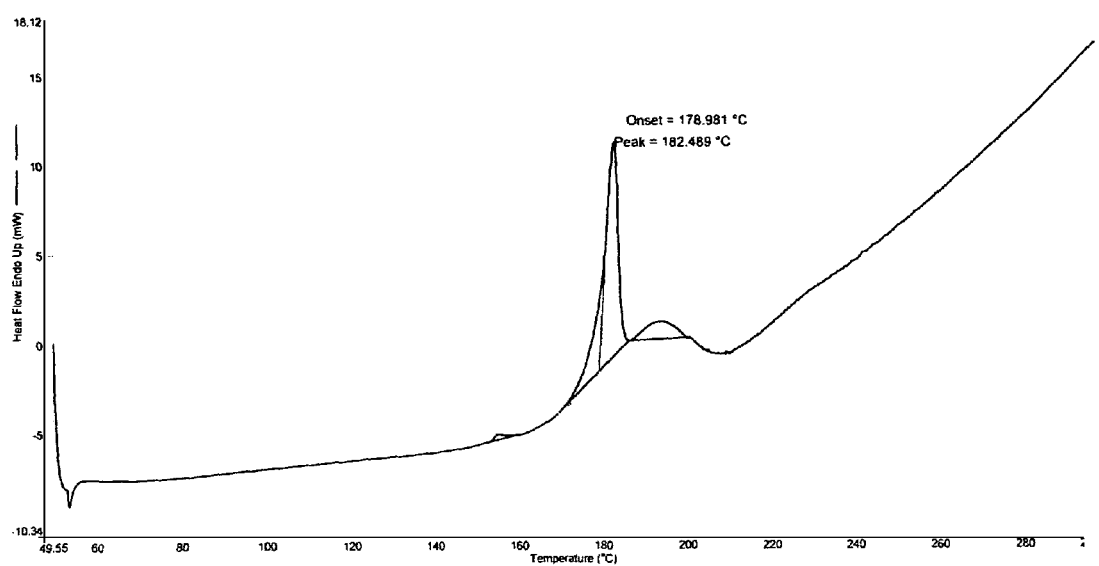
FIG. 2 is a Differential scanning calorimetry of the crystalline form of compound of Formula (IIb1) according to the present invention.

As used herein, the term "CCI-779" refers to Rapamycin 42-ester with 3-hydroxy-2-(hydroxymethyl)-2-methylpropionic acid, commercially known as CCI-779. The term "TMEDA" refers to N,N,N,N'-tetramethylethylenediamine, the term "DMEDA" refers to N,N'-dimethylethylenediamine, the term "THF" refers to tetrahydrofuran, the term "DCM" refers to dichloro methane, the term "DMF" refers to dimethyl formamide, the term "DIPE" refers to di-isopropyl ether, the term "DMSO" refers to dimethyl sulfoxide, the term "DMA" refers to dimethylacetamide, the term "NMP" refers to N-methylpyrrolidone, the term "PTSA" refers to p-toluene sulfonic acid, the term "PPTS" refers to Pyridinium p-toluenesulfonate, the term "DMAP" refers to 4-(dimethylamino) pyridine, the term "TEA" refers to triethylamine.

The inventors have developed a process for the preparation of CCI-779 using novel intermediates of Formula (Ia). The process includes:

i) reacting rapamycin of Formula (R),

Formula (R)

with one or more suitable acylating agents in the presence of one or more suitable bases to give a compound of Formula (Ia);

Formula (Ia)

(ii) converting 31, 42-rapamycin diacetate of Formula (Ia) to 31-monoacetate of Formula (Ib) by using a suitable base and suitable solvent(s)

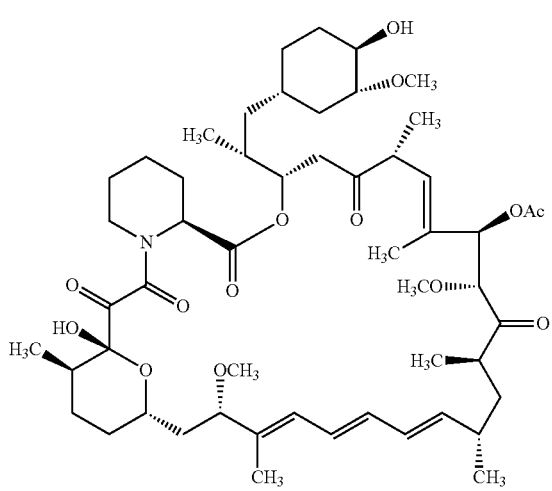

Formula (Ib)

(iii) selectively esterifying the 31-monoacetate of rapamycin of the compound of Formula (Ib) at 42-position to obtain a compound of Formula (Ic) by using suitable esterification reagents and suitable solvents; and

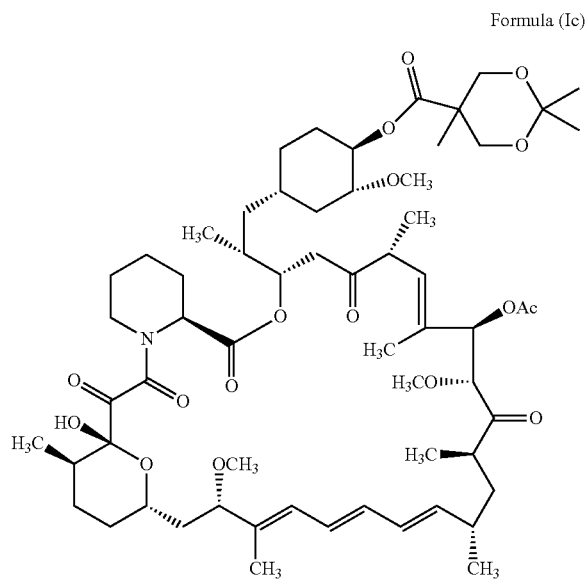

Formula (Ic)

(iv) deprotecting the 42-ester and 31-acetyl group of the compound of Formula (Ic) with suitable acids in suitable solvent to give CCI-779 of Formula (I).

In general, the reaction of rapamycin with suitable acylating agent may be carried out in the presence of a suitable base. The suitable acylating agents used may be selected from alkanoyl ($C_2$-$C_{10}$) halides, benzoyl halides including their mono- or disubstituted derivatives, wherein the substituents are selected from hydroxy, halogens, ($C_1$-$C_4$)alkyl, ($C_1$-$C_4$) alkoxy, or haloalkyl groups; or phenyl substituted alkanoyl halides wherein the alkanoyl portion has two to ten carbon atoms and the phenyl is unsubstituted or mono- or di-substituted with halogens, hydroxy, ($C_1$-$C_4$)alkyl, ($C_1$-$C_4$)alkoxy, or haloalkyl groups or derivatives thereof or mixtures thereof.

Suitable bases which can be used at step (i) may include one or more of triethyl amine; pyridine, DMAP, and the like or mixtures thereof.

The conversion of 31, 42-rapamycin diacetate of Formula (Ia) to 31-monoacetate of Formula (Ib) may be carried out using a suitable base and suitable solvents.

Suitable bases which can be used at step (ii) may be selected from suitable carbonates, bicarbonates, alkali hydroxides, ammonia, ammonium carbonate, ammonium acetate, ammonium halide, and the like, or mixtures thereof.

Suitable solvents which can be used at step (ii) may include one or more of alcohols such as methanol, ethanol, t-butanol, and the like; ethers such as THF, DIPE, 2-methyl tetrahydrofuran; esters like ethyl acetate, isopropyl acetate; hydrocarbons such as toluene; halogenated hydrocarbons such as DCM; DMF, DMSO, DMAc, NMP, acetonitrile, and the like, or mixtures thereof.

The esterification of 31-monoacetate of Formula (Ib) may be carried out by using suitable esterification reagents in one or more suitable solvents.

Suitable esterification reagents which can be used at step (iii) may include one or more of 2,4,6-trichlorobenzoic 2,2, 5-trimethyl-1,3-dioxane-5-carboxylic anhydride, methyl 2,2, 3,3,6,9,9,10,10-nonamethyl-4,8-dioxa-3,9-disilaundecane-6-carboxylate, and the like or derivatives thereof, or mixtures thereof.

Suitable solvents which can be used at step (iii) may include one or more of to ethers such as THF, DIPE, 2-methyl tetrahydrofuran; esters like ethyl acetate, isopropyl acetate; hydrocarbons such as toluene; halogenated hydrocarbons such as DCM; DMF, DMSO, DMAc, NMP, acetonitrile, and the like, or mixtures thereof.

The deprotection of 42-ester, 31-acetyl group of the compound of Formula (Ic) may be carried out by using suitable acid and a suitable solvent to give CCI-779 of Formula (I).

Suitable solvents which can be used at step (iv) may include one or more of ethers such as THF, DIPE, 2-methyl tetrahydrofuran; esters like ethyl acetate, isopropyl acetate; hydrocarbons such as toluene; halogenated hydrocarbons such as DCM; DMF, DMSO, DMAc, NMP, acetonitrile, and the like, or mixtures thereof.

Suitable acid which can be used at step (iv) may include one or more of sulphuric acid, hydrochloric acid, phosphoric acid, acetic acid, PTSA, PPTS, and the like, or mixtures thereof.

In one aspect there is provided a novel intermediate of Formula (Ia), which can be used in the preparation of compound of Formula (I).

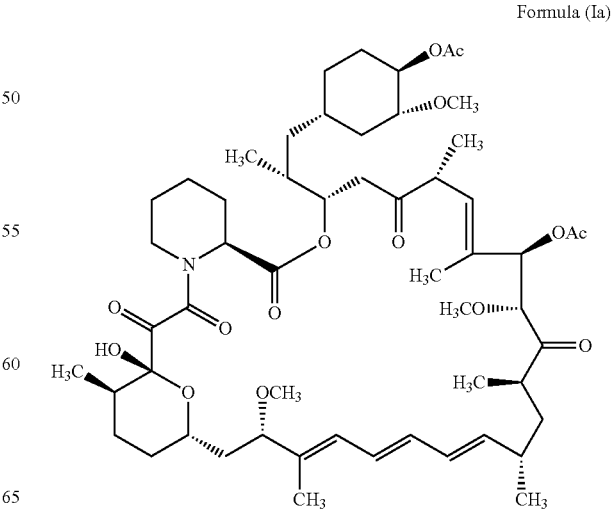

Formula (Ia)

In another aspect, there is provided a process for the preparation of 42-ester of the rapamycin, CCI-779. The process includes the following steps:

(i) reacting 2,2-bis(hydroxymethyl)propionic acid of Formula (A),

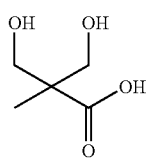

Formula (A)

with a suitable ketal of Formula (IIa) in the presence of a suitable acid catalyst to obtain a compound of Formula (IIb), Formula (IIa)

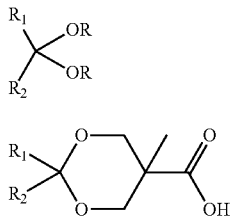

Formula (IIb)

wherein 'R' is selected from lower alkyl groups; and $R_1$ and $R_2$ independently represents $C_1$ to $C_{10}$ alkyl, $C_5$ to $C_{10}$ aryl groups, or $R_1$ and $R_2$ together with the carbon atom to which they are attached forms a $C_4$-$C_{10}$ cyclic ring, optionally substituted with to one or more groups selected from halogens, hydroxy ($C_1$-$C_4$)alkyl, ($C_1$-$C_4$)alkoxy, or haloalkyl groups, or bicyclic rings which may further be optionally substituted with one or more groups selected from halogens, hydroxy, ($C_1$-$C_4$)alkyl, ($C_1$-$C_4$)alkoxy, or haloalkyl groups, or tricyclic ring optionally substituted with one or more groups selected from halogens, hydroxy, ($C_1$-$C_4$)alkyl, ($C_1$-$C_4$)alkoxy, or haloalkyl groups.

Examples of suitable bicyclic groups as substituents on either $R_1$ or $R_2$ include camphor, substituted camphor and the like. Examples of suitable tricyclic groups as substituents on either $R_1$ or $R_2$ include fluorenone and substituted fluorenone and the like.

(ii) reacting the compound of Formula (IIb), with one or more suitable acylating agents in the presence of one or more suitable bases to form a mixed anhydride of a compound of Formula (IIc), wherein $R_1$ and $R_2$ are as defined above;

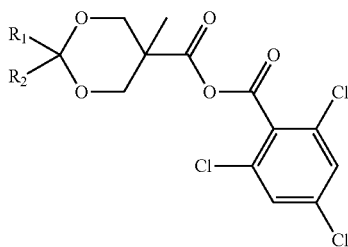

Formula (IIc)

(iii) reacting the compound of Formula (IIc) with rapamycin or 31-protected rapamycin in the presence of one or more suitable bases to give a suitably protected 42-ester of rapamycin of a compound of Formula (IId), wherein $R_1$ and $R_2$ are as defined above and 'P' is either H or a suitable protecting group; and Formula (IId)

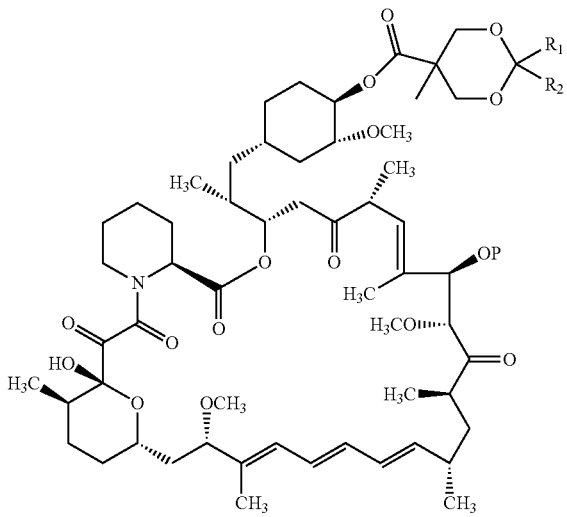

(iv) hydrolyzing the compound of Formula (IId) with a suitable acid to obtain the CCI-779 of the compound of Formula (I).

In general, the reaction of 2,2-bis(hydroxymethyl)propionic acid of Formula (A) with a suitable ketal of Formula (IIa) may be carried out in the presence of a suitable acid catalyst in a suitable solvent to get a compound of Formula (IIb), wherein R, $R_1$ and $R_2$ are as defined above.

Suitable acid catalyst which can be used at step (i) may include one or more of suitable organic acids such as PTSA, PPTS; inorganic acids $H_2SO_4$, HCl, $H_3PO_4$, and the like.

Suitable solvents which can be used at step-(i) may include one or more of ethers such as THF, DIPE, 2-methyl tetrahydrofuran, ethyl ether, tert. butyl methyl ether, dioxane; esters like ethyl acetate, isopropyl acetate; hydrocarbons such as toluene, benzene, hexane, cyclohexane; halogenated hydrocarbons such as DCM, chloroform; DMF, DMSO, DMAc, NMP, acetonitrile, and the like, or suitable mixtures thereof.

The reaction of the compound of Formula (IIb) with suitable acylating agent may be carried out in the presence of a suitable base to form a mixed anhydride of a compound of Formula (IIc), wherein $R_1$ and $R_2$ are as defined above.

Suitable acylating agent which can be used at step (ii) may include one or more of 2,4,6-trichloro benzoyl chloride and benzyl chloride, or derivatives thereof, or mixtures thereof.

Suitable bases which can be used at step (ii) may include one or more of suitable organic bases such as triethyl amine, TMEDA, DMEDA, pyridine; suitable inorganic bases such as alkali metal carbonates, and the like, or mixtures thereof.

Optionally, the mixed anhydride of the compound of Formula (IIc) formed in step-2 may be used in situ for the subsequent step.

The reaction of the compound of Formula (IIc) with rapamycin or 31-protected rapamycin may be carried out in the presence of a suitable base and in a suitable solvent to give a suitably protected 42-ester of rapamycin (IId), wherein $R_1$ and $R_2$ are as defined above and 'P' is either H or a suitable protecting group.

Suitable protecting groups which may be used are those known in the art, such as those disclosed in for example, in Protection and Deprotection of hydroxyl group in Text book—Title: *Protective Groups in Organic Synthesis, 3rd Edition*, John Wiley and Sons, By—T. W. Greene and Peter G. M Wuts).

Suitable bases which can be used at step (iii) may include one or more of suitable organic bases such as triethylamine, TMEDA, DMEDA, pyridine, N-methyl imidazole, DMAP, or suitable inorganic bases such as alkali metal carbonates, bicarbonates, and the like, or mixtures thereof.

Suitable solvents which can be used at step (iii) may include one or more ethers such as THF, DIPE, 2-methyl tetrahydrofuran, diethyl ether, tert. butyl methyl ether, dioxane; esters like ethyl acetate, isopropyl acetate; hydrocarbons such as toluene, benzene, hexane, cyclohexane; halogenated hydrocarbons such as DCM, chloroform; DMF, DMSO, DMAc, NMP, acetonitrile, and suitable mixtures thereof.

Hydrolysis of the compound of Formula (IId) may be performed using mild acidic conditions. Thus, the selected organic solvent may be mixed with dilute inorganic acids, such as $H_2SO_4$, HCl, $H_3PO_4$, or suitable organic acids such as acetic acid, PTSA, PPTS, and the like.

Suitable dilute inorganic acids concentrations range from about 0.1 N to about 3 N, 0.2 N to about 2 N, or about 0.5 N. This step may be carried out at a pH of from about 5 to about 6.

Suitable solvents which can be used at step (iii) may include one or more of $C_1$-$C_5$ alcohols, ethers such as THF, DIPE, 2-methyl tetrahydrofuran, ethyl ether, tert. butyl methyl ether, dioxane; esters like ethyl acetate, isopropyl acetate; hydrocarbons such as toluene, benzene, hexane, cyclohexane; halogenated hydrocarbons such as DCM, chloroform; DMF, DMSO, DMAc, NMP, acetonitrile, and the like, or suitable mixtures thereof.

Suitable solvents which can be used at step (iv) may include one or more of ethers such as THF, DIPE, 2-methyl tetrahydrofuran; esters like ethyl acetate, isopropyl acetate; hydrocarbons such as toluene; halogenated hydrocarbons such as DCM; DMF, DMSO, DMAc, NMP, acetonitrile, and the like, or mixtures thereof.

Suitable acid which can be used at step (iv) may include one or more of sulphuric acid, hydrochloric acid, phosphoric acid, acetic acid, PTSA, PPTS, and the like, or mixtures thereof.

In another aspect there are provided novel intermediates of Formula (IIb), (IIc) and (IId), which can be used in the preparation of the compound of Formula (I).

In one aspect there is provided a process for the preparation of the novel intermediate of the compound of Formula (IIa). The process includes, reacting the compound of Formula (III), wherein $R_1$ and $R_2$ are as defined above;

Formula (III)

with a compound of formula (IV),

Formula (IV)

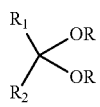

wherein R is lower alkyl, in the presence of a suitable acid catalyst and in a suitable solvent to obtain a compound of Formula (IIa).

Suitable acid catalyst, which can be used, may include one or more of suitable organic acids, such as PTSA, PPTS; inorganic acids such as $H_2SO_4$, HCl, $H_3PO_4$, $HPF_6$, $HClO_4$, and the like.

Suitable solvents, which can be used, may include one or more of ethers such as THF, DIPE, 2-methyl tetrahydrofuran, ethyl ether, tert. butyl methyl ether, dioxane; alcohols such as methanol, ethanol; esters like ethyl acetate, isopropyl acetate; hydrocarbons such as toluene, benzene, hexane, cyclohexane; halogenated hydrocarbons such as DCM, chloroform; DMF, DMSO, DMAc, NMP, acetonitrile, and the like, or suitable mixtures thereof.

Suitable substitutions on $R_1$ and $R_2$, which can be used for Formula (IIa) include those given in Table 1 below:

Formula (IIa)

R is methyl or ethyl

TABLE 1

| Formula (IIa) | $R_1$ and $R_2$ |
|---|---|
| II a1 | Camphor |
| II a2 | 9-Fluorenone |
| II a3 | & |
| II a4 | —Cl & —Cl |
| II a5 | —$(CH_2)_5$— |
| II a6 | —$(CH_2)_6$— |
| II a7 | —$(CH_2)_7$— |

Suitable groups and substituents on the groups may be selected from those described anywhere in the specification. Particularly useful compounds may be selected from:

IIa1

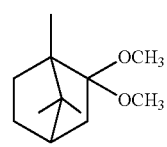

-continued

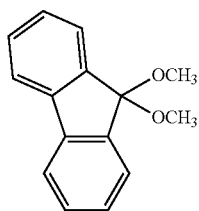
IIa2

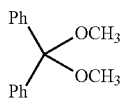
IIa3

In another aspect there is provided a process for the preparation of the novel intermediate of the compound of Formula (IIb).

The process includes reacting 2,2-bis(hydroxymethyl)propionic acid of formula (A),

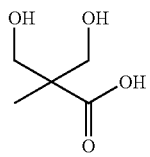
Formula (A)

with a suitable ketal of Formula (IIa),

Formula (IIa)

in the presence of a suitable acid catalyst in one or more suitable solvents to obtain a compound of Formula (IIb),

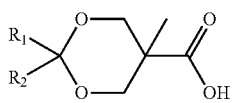
Formula (IIb)

wherein R is selected from lower alkyl; $R_1$ and $R_2$ are as defined above;

Suitable acid catalysts which can be used may include one or more of suitable organic acids such as PTSA, PPTS; or inorganic acids $H_2SO_4$, HCl, $H_3PO_4$, and the like.

Suitable solvents which can be used may include one or more of ethers such as THF, DIPE, 2-methyl tetrahydrofuran, ethyl ether, tert. butyl methyl ether, dioxane; esters like ethyl acetate, isopropyl acetate; hydrocarbons such as toluene, benzene, hexane, cyclohexane; halogenated hydrocarbons such as DCM, chloroform; DMF, DMSO, DMAc, NMP, acetonitrile, and the like, or mixtures thereof.

Suitable substitutions on $R_1$ and $R_2$, which can be used for Formula (IIb) include those given in Table 2 below:

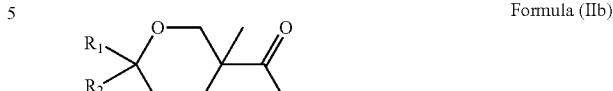
Formula (IIb)

TABLE 2

| Formula (IIb) | $R_1$ and $R_2$ |
|---|---|
| II b1 | Camphor |
| II b2 | 9-Fluorenone |
| II b3 | ![phenyl] & ![phenyl] |
| II b4 | ![4-Cl-phenyl] & ![4-Cl-phenyl] |
| II b5 | —(CH$_2$)$_5$— |
| II b6 | —(CH$_2$)$_6$— |
| II b7 | —(CH$_2$)$_7$— |

Suitable groups and substituents on the groups may be selected from those described anywhere in the specification: Particularly useful compounds may be selected from:

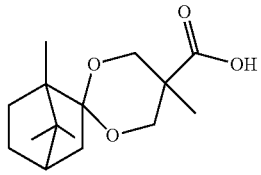
IIb1

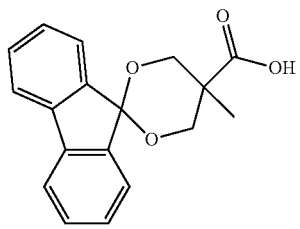
IIb2

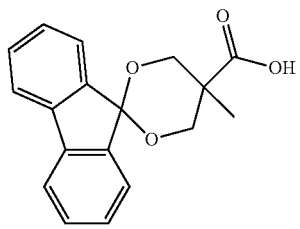
IIb3

The compound of Formula (IIb1) obtained according to the process of the present invention may be characterized by an XPRD pattern substantially in accordance with the pattern depicted in FIG. 1.

It may also be characterized by XPRD peaks at about 11.7, 16.17, 16.55, 17.19, 17.69, 19.29°±0.2 degrees 2θ. The crystalline form may further be characterized by additional XPRD peaks at about 9.56, 10.33, 11.70, 13.46, 20.85, 22.50, 25.65, 32.97°±0.2° degrees 2θ.

The crystalline form of the compound of Formula (IIb1) may be further characterized by a DSC comprising onset peaks at about 178° C.±2° C. and about 182° C.±2° C.

In another aspect there is provide a process for the preparation of the novel intermediate of the compound of Formula (IIc).

The process includes reacting a compound of Formula (IIb) with suitable acylating agents in the presence of a suitable base to form a mixed anhydride of the compound of Formula (IIc), wherein $R_1$ and $R_2$ are as defined above.

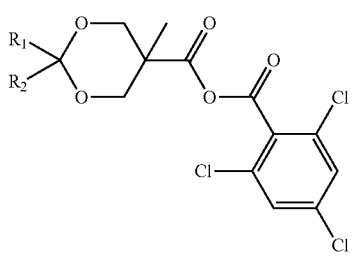

Formula (IIc)

Suitable acylating agents which can be used may include one or more of 2,4,6-trichloro benzoyl chloride and benzyl chloride, or derivatives thereof, or mixtures thereof.

Suitable bases which can be used may include one or more of suitable organic bases, such as triethylamine, TMEDA, DMEDA, pyridine; suitable inorganic bases, such as alkali metal carbonates, and the like, or mixtures thereof.

Optionally, the mix anhydride of the compound of Formula (IIc) formed may be used in situ for the subsequent step.

Suitable substitutions on $R_1$ and $R_2$, which can be used for Formula (IIc) include those given in Table 3 below:

TABLE 3

| Sr. No. | $R_1$ and $R_2$ |
|---------|-----------------|
| II c1   | Camphor         |
| II c3   | —⟨phenyl⟩ & —⟨phenyl⟩ |

Suitable groups and substituents on the groups may be selected from those described anywhere in the specification. Particularly useful compounds may be selected from:

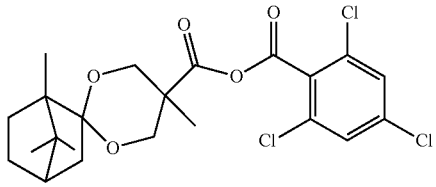

IIc1

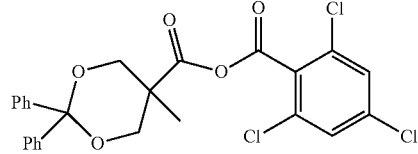

IIc3

In another aspect there is provided a process for the preparation of the novel intermediate of the compound of Formula (IId).

The process includes reacting a compound of Formula (IIc) with rapamycin or 31-protected rapamycin in the presence of a suitable base and in a suitable solvent to give a suitably protected 42-ester of rapamycin (IId), wherein $R_1$ and $R_2$ are as defined above and 'P' is either H or a suitable protecting group;

Suitable bases which may be used include one or more of suitable organic bases, such as trialkyl amines, triethyl amine, TMEDA, DMEDA, pyridine, N-methyl imidazole, DMAP, or suitable inorganic bases such as alkali metal carbonates, and the like, or mixtures thereof.

Suitable solvents which may be used include one or more ethers such as THF, DIPE, 2-methyl tetrahydrofuran, ethyl ether, tert. butyl methyl ether, dioxane; esters like ethyl acetate, isopropyl acetate; hydrocarbons such as toluene, benzene, hexane, cyclohexane; halogenated hydrocarbons such as DCM, chloroform; DMF, DMSO, DMAc, NMP, acetonitrile, and suitable mixtures thereof.

Suitable substitutions on $R_1$ and $R_2$, and P which can be used for Formula (IId) include those given in Table 4 below:

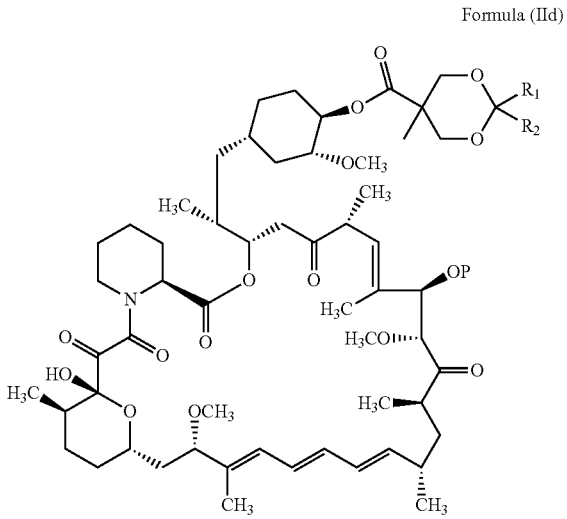

Formula (IId)

TABLE 4

| Formula (IIa) No. | R₁ and R₂ | P (P = Protecting group) |
|---|---|---|
| II d1 | Camphor | P = H |
| II d2 | 9-Fluorenone | P = H |
| II d3 | (tolyl) & (tolyl) | P = H |
| II d4 | (4-Cl-tolyl) & (4-Cl-tolyl) | P = H |
| II d5 | —(CH₂)₅— | P = H |
| II d6 | —(CH₂)₆— | P = H |
| II d7 | —(CH₂)₇— | P = H |
| II d8 | Camphor | P = -OAc |
| II d9 | Camphor | P = Trimethylsilyl |
| II d10 | (phenyl) & (phenyl) | P = Trimethylsilyl |

Suitable groups and substituents on the groups may be selected from those described anywhere in the specification. Particularly useful compounds may be selected from:

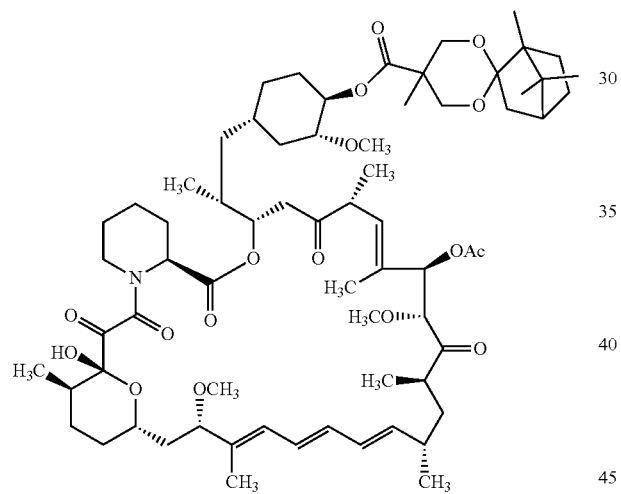

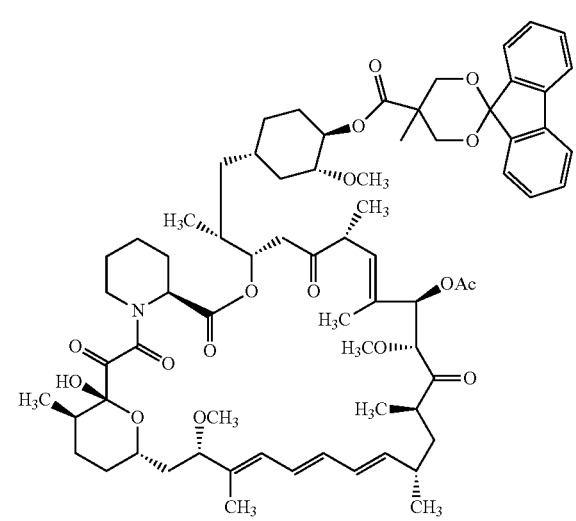

Figure 3:
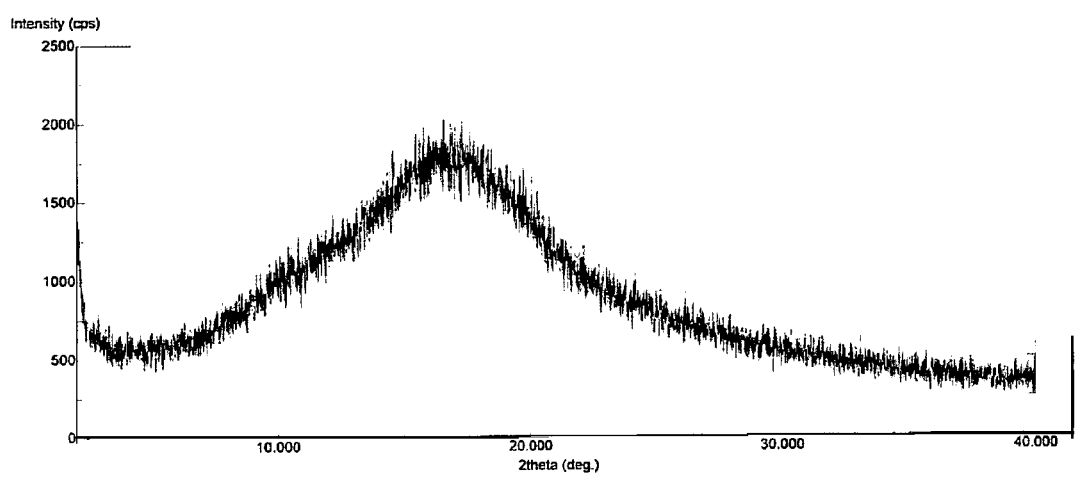
FIG. 3 is a powder X-ray diffraction (XRPD) pattern of compound of Formula (I) according to the present invention.

The compound of Formula (I) prepared by the processes of the invention may be obtained in an amorphous form. It may be characterized by an XPRD as depicted in FIG. 3.

In one aspect there is provided a pharmaceutical composition that includes a therapeutically effective amount of the CCI-779 prepared by any of the processes disclosed in the present invention; and one or more pharmaceutically acceptable carriers, excipients or diluents The CCI-779 of Formula (I) may be formulated into ordinary dosage forms such as, for example, tablets, capsules, pills, solutions, etc. In these cases, the medicaments can be prepared by conventional methods with conventional pharmaceutical excipients.

In a further aspect, the product obtained by any one of the processes disclosed may be further or additionally purified by Preparative HPLC Purification.

The Preparative HPLC may be carried out on either a Knauer or a Shimadzu model LC-8A liquid chromatograph. A solution of CCI-779 may be injected into YMC AQ ODS (50 mm-250 mm) column and eluted using a isocratic of 0.1% acetic acid in water:MeCN (65:35). A flow rate of 100 mL/min with effluent UV detection at 278 nm. The desired product may be eluted well separated from impurities, typically after 20-25 min, and may be collected in different 40-45 mL fractions manually. The fractions may be monitored by HPLC and >93% pure fractions may be collected. MeCN may be evaporated under vacuum. The desired product may be obtained as an amorphous white powder by lyophilization.

Analytical Processes:
i) The complete x-ray powder spectrum, which was recorded with a Rigaku multiflex 2.0 Kilowatt X-ray powder diffractometer model using copper radiation. The X-ray diffraction pattern was recorded by keeping the instrument parameters listed below:
X-ray: Cu/40 kv/30 mA, Diverging slit: 1°, Scattering slit: 1°, Receiving slit: 0.15 mm, Monochromator RS: 0.8 mm, Counter: Scintillation counters;
Scan mode: Continuous, Scan speed: 4.000 deg./min., Sampling width: 0.010°, Scan axes: 2 theta vs CPS, Scan range: 4° to 40.0°, Theta offset: 0.000.
ii) Differential scanning calorimetric analysis was carried out in a DSC-60 model from Shimadzu (S/W: TA-60WS Aquisition version 2.1.0.0) by keeping following parameters,
Sample Size Approx. 1-2 mg, Sample Pans: Hermetic/Crimping Pans,
Start Temperature: 50° C., End Temperature: 300° C., Rate of Heating: 10° C./min., Purge
Gas: Nitrogen, Flow rate: 20 ml/min
iii) The infrared (IR) spectrum has been recorded on a Shimadzu FTIR-8400 model spectrophotometer, between 450 $cm^{-1}$ and 4000 $cm^{-1}$, with a resolution of 4 $cm^{-1}$ in a KBr pellet.

The invention is further illustrated by the following examples which are provided to be exemplary of the invention and do not limit the scope of the invention. While the present invention has been described in terms of its specific embodiments, certain modifications and equivalents will be apparent to those skilled in the art and are intended to be included within the scope of the present invention.

EXAMPLE-1

Preparation of 2,2,5-trimethyl-[1,3]dioxane-5-carboxylic acid

In a round bottom flask (5 g) 1,3 dihydroxy 2-methyl 2-propionic acid, (33 mg) PTSA and 15 ml benzene was taken and it was refluxed. Subsequently, 5.81 g (1.5 equiv.) dimethoxy propane diluted with benzene was added dropwise under Dean Stark and continuous removal and addition of benzene up to 2 hr. After that (1.98 g) dimethoxy propane diluted with benzene was added and reaction mixture was stirred for 1 hr. Solid was obtained at 25° C. and was washed with benzene, excess benzene was distilled. Solid obtained was further purified by hexane.
Wt-6.3 g (96.9%)

EXAMPLE-2

Preparation of 31, 42 diacetate of rapamycin. Formula-(Ia)

(1 g) rapamycin was dissolved in 6 ml pyridine and the reaction mixture was cooled to 0-5° C. and 6 ml acetic anhydride was added at 0-5° C. The reaction mixture was stirred at 25° C. for 24 hr. After completion of the reaction water was added till white solid precipitate was obtained. Subsequently, precipitate was stirred at 25-30° C. for 1 hr and was filtered. The solid mass was washed with water. Dry it till constant weight.
Weight: 1.06 g (97% Yield),
Melting point=92-94° C.

$$ESIMS = 997.79[M^+], 1015.86[M + NH_3]^+,$$
$$1021.7[M + Na]^+ (+ve \text{ mode})$$
$$= 996.88[M - 1]^+ (-ve \text{ mode})$$

$^1$H NMR (CDCl$_3$) (400 MH$_Z$): 2.09-2.06 (d, 6H).

EXAMPLE-3

Preparation of 31-Monoacetate of rapamycin. Formula-(Ib)

(250 mg) of 31, 42 diacetate of rapamycin [Ia] was dissolved in 6 ml methanol and 120 mg (5 equiv.) of ammonium carbonate dissolved in water, was added and the reaction mixture was stirred for 3.5 hr at 25-30° C. Further 120 mg of ammonium carbonate was added and reaction mixture was stirred for 3.5 hr at 25-30° C. Again 120 mg ammonium carbonate was added and reaction mixture was stirred for 16 hr at 25-30° C. Methanol was distilled on rotavapour. Into the reaction mass water was added and extracted it by ethyl acetate and then ethyl acetate layer washed by brine and water. Dried it by adding sodium sulfate and concentrate it to obtain yellow colored sticky compound.
Weight: 220 mg (92%) Then add 25 ml n-hexane, mixture was stirred for 30 min.
Filtered it, wash the solid mass with n-hexane to get a light yellow solid product.
Weight: 135 mg $$ESIMS = 955.98[M^+], 979.11[M + Na]^+ (+ve \text{ mode})$$
$$= 954.85[M - 1]^+ (-ve \text{ mode})$$

$^1$H NMR (400 MHz) CDCl$_3$: 2.06 (s, 3H).

EXAMPLE-4

Preparation of 31-acetate, 42-ester of rapamycin with 2,2,5 trimethyl-[1,3 dioxane]-5-carboxylic acid. Formula-(Ic)

(100 mg) of 2,2,5-Trimethyl-[1,3]dioxane-5-carboxylic acid [III] was dissolved in 2 ml dichloromethane and cooled to 0-10° C. (121 mg) triethyl amine was diluted with 0.5 ml dichloromethane and (139 mg) 2,4,6-trichloro benzoyl chloride diluted with 0.5 ml dichloromethane was added into cooled reaction mixture and was stirred at 25° C. for 4 hr. Excess of solvent was distilled. Further the reaction mixture was dissolved in 20 ml toluene and was stirred it for 10 min. at 0-10° C. The reaction mixture was filter and washed with toluene. Then this filtrate was cooled at 0-10° C. in ice bath and 29.9 mg N,N-Dimethyl amino pyridine (DMAP) was added and stirred 5 min. Subsequently, (50 mg) monoacetate of rapamycin [Ib] dissolved in 3 ml toluene was added and stirred for 17 hr at 25-30° C. After completion of the reaction the reaction mass was dumped in to water. The layer was separated and washed the organic layer with brine solution and water. Dried it by adding sodium sulfate and distilled to obtain Yellow colored sticky compound i.e 31-acetate, 42-ester of rapamycin with 2,2,5 tri methyl-[1,3 dioxane]-5-carboxylic acid [Ic].

Weight: 76 mg.
ESI MS=1134.67[M+Na]$^+$, 1151.4 [M+K] (+ve mode).

EXAMPLE-5

Preparation of 31-acetate, 42-ester of Rapamycin with 2,2,5 trimethyl-[1,3 dioxane]-5-carboxylic acid. Formula-(Ic)

(300 mg) of 2,2,5-Trimethyl-[1,3]dioxane-5-carboxylic acid was dissolved in 4 ml DCM and cooled the reaction mixture to 0-10° C. Subsequently, (365 mg) TEA is diluted with DCM and (420 mg) 2,4,6-trichloro benzoyl chloride diluted with DCM is added into cooled reaction mixture and is stirred at 25° C. for 2.5 hr. Excess of solvent was distilled with one washing of DCM. Further the reaction mixture was dissolved in toluene and cooled at 0-10° C. and (13.6 mg) DMAP was added and stirred for 5 min. Then into it (165 mg) of 31-monoacetate of Rapamycin dissolved in toluene was added. Further the reaction mixture was stirred for 18 hr at 25° C. and reaction mass was dumped into water. Toluene layer was separated, washed by brine solution, dried and distilled to obtain 31-acetate, 42-ester of Rapamycin with 2,2,5 trimethyl-[1,3 dioxane]-5-carboxylic acid, Wt-244 mg.

EXAMPLE-6

Preparation of CCI-779. Formula-(I)

(163 mg) of 31-acetate, 42-ester of rapamycin with 2,2,5 trimethyl-[1,3 dioxane]-5-carboxylic acid [Ic] was dissolved in 1.6 ml THF and cooled to 0-5° C. 0.8 ml 2N sulphuric acid was added into the reaction mixture. The reaction mixture was stirred at 0-5° C. for 30 min. and at 25-30° C. for 23 hr. After completion of the reaction ethyl acetate and brine solution was added. The layer was separated and organic layer wash first by sodium bicarbonate solution and then by water, dry it by adding sodium sulfate and concentrate it on rotavapour to get yellow colored oily product.

Weight: 190 mg.

$$ESI\text{-}MS = 1029.28[M+]^+ (+ve \text{ mode})$$
$$= 1028.2[M-1]^+ (-ve \text{ mode})$$

EXAMPLE-7

Preparation of 2,2-diethoxy-1,7,7-trimethyl bicyclo-[2.2.1]heptane

To a flask with reflux condenser, (25 g) camphor and 50 ml absolute ethanol was taken. (36.45 g) (1.5 eq.) triethyl orthoformate and crystals of p-toluenesulfonic acid was added into the reaction mixture. The reaction mixture was heated to reflux overnight. The reaction mixture was cooled and concentrated on rotavapour and was washed with 10% potassium hydroxide solution. Extract it with dichloromethane and concentrated the organic layer on rotavapour, yellow colored liquid product was obtained. 38. g (Quantitative)

ESI-MS=226.67 (M)$^+$, 227.17 (M+1) (negative mode).

EXAMPLE-8

Preparation of 1,1-diethoxy cyclohexane. Formula-(IIa5)

In a round bottom flask 6 g (6.4 ml) Cyclohexanone, a pinch of p-toluene sulfonic acid and 10 ml absolute ethanol was taken. Stirred the mixture at R.T. for 5 min. Then add to it 18.12 g (20.3 ml) triethyl orthoformate and stir for 3 hr at R.T. Then distilled on rotavapour to get a thick mass. Add to it 30 ml water and extract with (25 ml×ethyl acetate, wash the organic layer with water, dried it by adding sodium sulfate and concentrate it on rotavapour to give a colorless liquid product.

Weight: 3.3 g (31.3% Yield)
G.C. purity=53%

EXAMPLE-9

Preparation of 3-methyl-1,5-dioxaspiro[5,5]undecane]-3-carboxylic acid. Formula-(IIb5)

In a round bottom flask, (2 g) diethoxy cyclohexane [IIa5] and 1.5 ml toluene were taken. Pinch of p-toluene sulfonic acid was added in to the reaction mixture and the reaction mixture was heated under reflux 120-130° C. (1 g) (1.5 equiv.) 3-hydroxy-2-(hydroxymethyl)-2-methylpropanoic acid was added into the reaction mixture at reflux temperature. Continuous removal and addition of toluene was done upto 2.5 hr. Then concentrate it on rotavapour to get brown colored viscous compound.

Wt-1.65 gm (Quantitative)
G.C. purity=63%.
ESI MS=213.35[M−1]$^+$ (−ve mode).

EXAMPLE-10

Preparation of Dimethoxy diphenylmethane. Formula-(IIa3)

In a round bottom flask, (10 g) Benzophenone in 20 ml methanol was taken. 12 ml (2 equiv.) trimethyl orthoformate was added into the reaction mixture in a single lot and the reaction mixture was stirred at 25-30° C. 3-4 drop perchloric acid (HClO$_4$ as a catalyst) was added and reflux it for 9 hr. After completion of the reaction, the reaction mass was dumped into water. Subsequently, the reaction mass was stirred for 15 min, filtered it and wash the solid mass with water to obtain white solid product.

Weight: 11.6 g (92.61%)
HPLC purity=92.68%
ESI MS=196.8 [M-OMe]$^+$ (−ve mode)
M.P.=110-112° C.
$^1$H NMR (400 MH$_z$) CDCl$_3$: 7.5-7.4 (m, 4H), 7.3-7.26 (m, 4H), 7.22-7.18 (m, 2H), 3.12 (s, 6H).
$^{13}$C NMR (400 MHz) (CDCl$_3$): 142.5, 128.1, 127.5, 127.0, 102.9, 49.42

EXAMPLE-11

Preparation of 5-methyl-2,2-diphenyl-1,3-dioxane-5-carboxylic acid. Formula-(IIb3)

In a round bottom flask, (12 g) 3-hydroxy-2-(hydroxymethyl)-2-methylpropanoic acid and 35 ml toluene was taken.

(99.4 mg) p-toluene sulfonic acid was added into the reaction mixture at 25-30° C. temperature. The reaction mixture was heated at reflux temperature, and 20.5 g (1 equiv.) dimethoxy diphenylmethane [IIa3] in 35 ml toluene was added and it was further refluxed under dean stark. Continuous removal and addition of toluene done upto 3 hrs. Then reaction mixture was cooled at 25-30° C. and dumped into water. The reaction mixture was stirred at 20-30° C. and filter it and wash the solid mass with water to obtain white solid product.

Weight: 18.16 gm (69.4% Yield)
M.P.=195-197° C.

$$ESIMS = 298.9[M^+], 336.9[M+K]^+ (+ve \text{ mode})$$
$$= 296.8[M-1]^+ (-ve \text{ mode})$$

HPLC purity=94.5%. After Acid-Base to obtained 99.6% purity.

$^1$H NMR (400 MH$_Z$) CDCl$_3$: 7.52-7.5 (m, 2H), 7.45-7.32 (m, 2H), 7.39-7.35 (m, 2H), 7.31-7.3 (m, 1H), 7.29-7.28 (m, 2H), 7.26-7.22 (m, 1H), 4.32-4.29 (d, J=11.6 Hz, 2H), 3.78-3.75 (d, J=11.6 Hz, 2H), 1.19 (s, 3H).

I.R. (in KBr)=3059 cm$^{-1}$, 1707.66 cm$^{-1}$

EXAMPLE-12

Preparation of 42-ester of rapamycin with 5-methyl-2,2-diphenyl-1,3-dioxane-5-carboxylic acid. Formula-(IId3)

(81.4 mg) of 5-methyl-2,2-diphenyl-1,3-dioxane-5-carboxylic acid [IIb3] was dissolved in 2.2 ml dichloromethane and cooled at 0-10° C. (55.2 mg) triethyl amine was diluted with 0.068 ml dichloromethane and 42.6 mg 2,4,6-trichloro benzoyl chloride diluted with 0.068 ml dichloromethane was added into cooled reaction mixture and the reaction mixture was stirred at 0-5° C. for 3 hrs. Excess of solvent was distilled out and further the reaction mixture was dissolved in toluene and was stirred for 5 min. at 25-30° C. Filter it and wash with toluene. Then this filtrate was cooled at 0-10° C. in ice bath and (33 mg) N,N-Dimethyl amino pyridine (DMAP) was added and stirred for 5 min. Subsequently, (50 mg) rapamycin was dissolved in 2.5 ml toluene and added into the reaction mixture. Reaction mass was stirred for 3.5 hrs at 0-5° C., then it was stirred for 16 hrs at 25-30° C. After completion of the reaction the reaction mass was filtered and washed with toluene. Toluene layer was washed by water, NaHCO$_3$ solution and brine solution. Dried it by adding sodium sulfate and distilled to obtain yellow colored sticky mass of 42-ester of rapamycin.

Weight: 193 mg (Quantitative)

$$ESIMS = 1216.9[M+Na]^+ (+ve \text{ mode})$$
$$= 1193.8[M^+] (-ve \text{ mode})$$

HPLC purity=61.9%

EXAMPLE-13

Preparation of CCI-779. Formula-(I)

(40 mg) of 42-ester of rapamycin with 5-methyl-2,2-diphenyl-1,3-dioxane-5-carboxylic acid [IId3] was taken, 1 ml 80% acetic acid was added and the reaction mixture was stirred. Subsequently, the reaction mixture was heated to 60-80° C. and stirred for 19 hrs at 60-80° C. After completion of the reaction water was added, extracted by ethyl acetate, ethyl acetate layer was washed by Sodium bicarbonate solution, water and brine solution. Organic layer was separated, dried and concentrated to get yellowish sticky mass.

Weight: 31.7 mg. (91.9%) Then n-hexane was added, stirred for 15 min. filtered it, washed with n-hexane to get light yellowish Solid product.

Weight: 16.5 mg.

$$ESIMS = 1030.7[M^+] (+ve \text{ mode})$$
$$= 1030.5[M^+] (-ve \text{ mode})$$

EXAMPLE-14

Preparation of benzoic 5-methyl-2,2-diphenyl-1,3-dioxane-5-carboxylic anhydride

In a 25 ml round bottom flask, (200 mg) 5-methyl-2,2-diphenyl-1,3-dioxane-5-carboxylic acid [IIb3] was taken and dissolved in 5.5 ml dichloromethane and cooled at 0-10° C. (135 mg) triethyl amine was diluted with 0.3 ml dichloromethane and 0.12 ml benzoyl chloride diluted with 0.3 ml dichloromethane was added into cooled reaction mixture and the reaction mixture was stirred at 25-30° C. for 3 hr. After completion of the reaction dichloromethane and water were added, layer was separated. Organic layer was washed with water. Dry it by adding sodium sulfate and concentrate it on rotavapour to obtain white solid product.

Weight: 350 mg (Quantitative)
ESI MS=402.9[M$^+$], 419.9[M+NH$_3$]$^+$ (+ve mode).
I.R. (in KBr)=1786 cm$^{-1}$, 1730 cm$^{-1}$

EXAMPLE-15

Preparation of rapamycin 42-ester with 5-methyl-2,2-diphenyl-1,3-dioxane-5-carboxylic acid. Formula-(IId3)

In a flask, (116 mg) Benzoic 5-methyl-2,2-diphenyl-1,3-dioxane-5-carboxylic anhydride was dissolved into 3.5 ml toluene. The reaction mass was cooled at 0-10° C. and subsequently (35 mg) N,N-dimethyl amino pyridine (DMAP) was added and stirred for 5 min. Then a solution of (66 mg) rapamycin in 4 ml toluene was added and further stirred for 7 hrs at 25-30° C. After completion of the reaction toluene and water were added, layer was separated. The toluene layer was washed with NaHCO$_3$ solution and water. Dry it by adding sodium sulfate and concentrate it on rotavapour to obtain yellow colored oily compound.

Weight: 145 mg (Quantitative)
ESI MS=1194.9 [M]$^+$ (+ve mode).

EXAMPLE-16

Preparation of CCI-779. Formula (I)

(136 mg) of rapamycin-42-ester with 5-methyl-2,2-diphenyl-1,3-dioxane-5-carboxylic acid [IId3] was dissolved in 2 ml THF and cooled to 0-5° C. 0.2 ml 2N hydrochloric acid was added and the reaction mixture was stirred at 25-30° C. for 24 hrs. Then it was concentrated on a rotavapour and the residue was dissolved in 2 ml ethyl acetate and subsequently, (80 mg) potassium hydrogen sulfate in 2.5 ml water was added. The reaction mixture was stirred at 25-30° C. for 24 hrs. After completion of reaction, reaction mass was dumped into water and extracted with ethyl acetate. The layers were separated, washed the organic layer with 10% $NaHCO_3$ solution and then water. It was dried over sodium sulfate. Concentrate it on rotavapor to obtain yellow colored oily compound.

Weight: 110 mg (Quantitative)
ESI-MS=1031.6 [M+1] (+ve mode).

EXAMPLE-17

Preparation of bis-(4-chlorophenyl)dimethoxymethane. Formula (IIa4)

In a round bottom flask, (2 g) 4,4'-dichlorobenzophenone in 4 ml methanol was taken. (1.75 ml) (2 equiv.) tri-methyl orthoformate was added into the reaction mixture and stirred at 25-30° C. Then 0.04 ml perchloric acid (as a catalyst) was added and refluxed for 7.5 hrs. After completion of the reaction ethyl acetate and $NaHCO_3$ solution were added and stirred for 10 min. Then layers were separated and washed the organic layer with water. Dry it over sodium sulfate. Concentrate it on rotavapor to obtain yellow colored liquid product Weight: 2.1 g (88.74% Yield)
HPLC purity=91.85%
to ESI-MS=266.9[M-OMe]$^+$
$^1$H NMR (400 MHz) $CDCl_3$: 7.41-7.38 (d, J=8.8 Hz, 4H), 7.41-7.39 (d, J=8.4 Hz, 4H), 3.09 (s, 6H).

EXAMPLE-18

Preparation of 2,2-bis(4-chloro phenyl)-5-methyl-1, 3-dioxane-5-carboxylic acid. Formula (IIb4)

In a round bottom flask, (0.9 g) 3-hydroxy-2-(hydroxymethyl)-2-methylpropanoic acid and (9.8 mg) p-toluene sulfonic acid and 2 ml toluene was taken. The reaction mixture was stirred at room temperature and subsequently 2 g (1 equiv) bis-(4-chlorophenyl)-dimethoxymethane [IIa4] diluted with 5 ml toluene was added through droping funnel. The reaction mixture was heated at reflux temperature and the water was removed azeotropically under Dean Stark. Continuous removal and addition of toluene was done up to 2 hrs. Then the reaction mixture was cooled at room temperature to obtain off white solid. It was filtered and washed with toluene and then water.

Weight: 1.3 g (52.54% Yield)
HPLC purity=96.4%
ESI MS=364.8[M−1]$^+$ (−ve mode)
M.P.=167-175° C.
I.R. (in KBr)=3369.75 cm$^{-1}$, 1708.9 cm$^{-1}$
$^1$H NMR (400 MHz) $CDCl_3$: 7.48-7.46 (d, J=8.0 Hz, 2H), 7.36-7.34 (d, J=8.0 Hz, 2H) 7.26-7.24 (d, J=8.0 Hz, 2H), 4.30-4.28 (d, J=11.6 Hz, 2H), 3.71-3.68 (d, J=11.6 Hz, 2H), 1.17 (s, 3H).

EXAMPLE-19

Preparation of rapamycin-42-ester with 2,2-bis(4-chloro phenyl)-5-methyl-1,3-dioxane-5-carboxylic acid Formula (IId4)

In a 50 ml round bottom flask, (50 mg) 2,2-bis(4-chloro phenyl)-5-methyl-1,3-dioxane-5-carboxylic acid [IIb4] was taken and 2 ml dichloromethane was added to form a clear solution. The reaction mass was cooled at 0-5° C. in ice bath and subsequently, (27.52 mg) triethyl amine in 0.25 ml dichloromethane was added drop wise under nitrogen atmosphere. (36.48 mg) 2,4,6-trichloro benzoyl chloride in 0.25 ml dichloromethane was then added drop wise at 0-5° C. and the reaction mass was stirred at 0-5° C. for about 2 hrs. It was concentrated on rotavapour, oily product was obtained, toluene was added into the reaction mass and stirred for 10 min. The reaction mass was filtered and washed the residue with toluene. The mother liquor was cooled at to 0-5° C., (16.62 mg) N,N-Dimethyl amino pyridine (DMAP) was added in single lot and subsequently the reaction mixture was added drop wise in to a solution of 49.73 mg rapamycin in 2 ml toluene. The reaction mass was stirred at room temperature over night. After completion of reaction filter the reaction mass and wash the toluene layer with 10% sodium bicarbonate solution then water and brine solution. It was concentrated on rotavapour when white solid product obtained.

Weight of 42-ester of rapamycin=95 mg (Quantitative)
ESI-MS=1280.9 $(M+NH_3)^+$

EXAMPLE-20

Preparation of CCI-779. Formula (I)

In a 25 ml round bottom flask, (68 mg) rapamysin-42-ester with 2,2-bis(4-chloro phenyl)-5-methyl-1,3-dioxane-5-carboxylic acid [IId4] was taken. 4 ml THF was added and the reaction mixture was cooled at 0 to 5° C. 0.18 ml 2N sulfuric acid was added drop wise in 15 minutes and the reaction mass was stirred at 25-30° C. for about 40 hrs. After completion of reaction dilute the reaction mass by adding brine and extract with ethyl acetate, the organic layer was washed with 5% sodium bicarbonate solution and then water and brine solution. It was concentrated on a rotavapor when oily product was obtained. This oily mass was stirred in cyclohexane, and remove the cyclohexane by filtration. The residue was concentrated till dryness to give white solid product. Purification of the crude CCI-779 is done by dissolving in acetone and then completely removing it on rotavapour. It was again dissolved in diethyl ether and precipitated by adding n-heptane drop wise to get white solid product by stirring at room temperature for about 2 hrs. It was filtered and washed the solid product with n-heptane.

Weight of CCI-779=65 mg (% Yield=Quantitative)
ESI-MS=1047.4 $(M+NH_3)^+$

EXAMPLE-21

Preparation of 1,1-dimethoxy-1,2,3,4-tetrahydronaphthalene

In a round bottom flask, (10 g) 1-tetralone in 20 ml methanol, 15 ml (2 equiv.) trimethyl orthoformate was taken and the mixture was stirred at room temperature. 0.2 ml hexafluoro phosphoric acid (catalytic amount) was added and the mixture was refluxed for 5.5 hrs. The mixture was then cooled at 25-30° C. After completion of reaction dilute the reaction mass by adding 10% $NaHCO_3$ solution and extract with ethyl acetate. The organic layer was washed with $NaHCO_3$ solution. Dry it by adding sodium sulfate, concentrate it on rotavapour to give dark brown colored oily product.

Weight: 11 g (83.64% Yield).

EXAMPLE-22

Preparation of 5-methyl-3'4'-dihydro 2'H-spiro[1,3]dioxane-2,1'-naphthalene]-5-carboxylic acid In a round bottom flask, 7.6 g 3-hydroxy-2-(hydroxymethyl)-2-methylpropanoic acid was taken and in to it (82 mg) p-toluene sulfonic acid as a catalyst and add 20 ml toluene were added. The reaction mixture was stirred at 25-30° C. Subsequently, (11 g) (1 equiv) 1,1-dimethoxy-1,2,3,4-tetrahydronaphthalene diluted with toluene was added and was refluxed using Dean stark apparatus. Continuous removal and addition of toluene done up to 4 hrs. Then the solution was cooled at 25-30° C. and toluene and water were added. Layer was separated; organic layer was dried by adding sodium sulfate, concentrate it on rotavapor to give brownish sticky compound. Wt-14.3 g (95.28%)

Then wash with n-hexane.

Weight: 11.7 g

ESI MS=262.9[$M^+$], 284.9[$M+Na$]$^+$ (+ve mode).

EXAMPLE-23

Preparation of 1,1-dimethoxy cycloheptane. Formula (IIa6)

To a flask with reflux condenser (5 g) cycloheptanone, and 10 ml methanol was taken. (10 ml) (2.0 eq.) trimethyl orthoformate and several crystals of p-toluenesulfonic acid were added in to the reaction mixture and the mixture was stirred at 25-30° C. to about 1.5 hrs. Color of the reaction mixture became pale yellow. Reaction was monitored by TLC. Then remove the methanol on rotavapour. Water was added in to the reaction mixture and extract with ethyl acetate. Organic layer was washed with 5% sodium bicarbonate solution then water and brine solution. Concentrate it on rotavapor yellow colored oily product obtained.

Weight: 4.25 g (60.27%)

ESI MS=126.8 [M-OMe] (+ve mode)

EXAMPLE-24

Preparation of 3-methyl-1,5-dioxaspiro[5.6]dodecane-3-carboxylic acid. Formula (IIb6)

In a round bottom flask, (3.394 g) 3-hydroxy-2-(hydroxymethyl)-2-methylpropanoic acid, (30 mg) p-toluene sulfonic acid and 10 ml toluene was taken and stirred it. Subsequently, (4 gm) 1,1-dimethoxy cycloheptane [IIa6] diluted with 7 ml toluene was added and reaction mixture was refluxed at 120-140° C. under Dean stark apparatus. 10 ml solvent was removed and then 5 ml toluene was added and reaction mixture was again stirred at 120-140° C. for 1.5 hrs. The reaction mixture was cooled at 25-30° C., filtered and washed the filtrate with water. Organic layer was dried by adding sodium sulfate, concentrate it on rotavapor to obtain light yellow oil.

Then n-hexane was added and stirred for 15 min, filter and washed the solid mass with n-hexane to get white solid product.

Weight: 210 mg

G.C. purity=96.77%

I.R. (in KBr)=3448.84 cm$^{-1}$, 1689.7 cm$^{-1}$ $$ESIMS = 228.9[M^+], 250.5[M + Na]^+ (ve \text{ mode})$$
$$= 226.9[M - 1]^+ (-ve \text{ mode})$$

$^1$H NMR (400 MHz) CDCl$_3$: 4.12-4.09 (d, J=12 Hz, 2H), 3.69-3.66 (d, J=12 Hz, 2H), 1.98-1.96 (m, 2H), 1.89-1.86 (m, 2H), 1.57-1.51 (m, 8H), 1.18 (s, 3H).

EXAMPLE-25

Preparation of Rapamycin-42-ester with 3-methyl-1,5-dioxaspiro[5.6]dodecane-3-carboxylic acid. Formula (IId6)

(125 mg) of 3-methyl-1,5-dioxaspiro[5.6]dodecane-3-carboxylic acid [IIb6] was dissolved in 3.7 ml dichloromethane and cooled to 0-5° C. (110 mg) triethyl amine was diluted with 0.5 ml dichloromethane and (133 mg) 2,4,6-trichloro benzoyl chloride diluted with 0.5 ml dichloromethane were added into cooled reaction mixture and was stirred at 0-5° C. for 2 hrs. Excess of solvent was distilled and further the reaction mixture was dissolved in 4 ml toluene and stirred for 10 min at 25-30° C. The reaction mixture was filtered and washed with 2 ml toluene. The filtrate was cooled at 18-20° C. and (66 mg) N,N-Dimethyl amino pyridine (DMAP) was added and stirred for 5 min. Then (200 mg) rapamycin dissolved in 7 ml toluene was added and stirred for 19 hrs at 25-30° C. The reaction mass was filtered, washed with toluene, toluene layer was washed by water, NaHCO$_3$ solution and brine solution. It was dried by adding sodium sulfate and concentrated to obtain yellow color oily product.

Weight: 307 mg (quanti.) Then n-hexane was added and stirred for 1 hr, filtered and washed the solid mass with n-hexane to get a white solid product.

Weight: 160 mg

ESI-MS=1141.3 (M+NH$_3$)$^+$

EXAMPLE-26

Preparation of CCI-779. Formula (I)

(160 mg) of 42-ester of rapamycin with 3-methyl-1,5-dioxaspiro[5.6]dodecane-3-carboxylic acid [IId6] was dissolved in 4 ml THF and was cooled it at 0-5° C. Subsequently, 0.5 ml 2N sulphuric acid was added and the reaction mass was stirred at 30-35° C. for 20 hrs. After completion of the reaction brine solution was added and extracted by ethyl acetate. Organic layer was separated and wash it with sodium bicarbonate solution and then by water. Dried by adding sodium sulfate and concentrate it on rotavapour to get colorless viscous oily product. Subsequently, n-hexane was added and stirred for 30 minute. White solid was precipitated, which was filtered, washed with n-hexane to get white solid product.

Weight: 114 mg.

ESI MS=1047.4 (M+NH$_3$)$^+$

EXAMPLE-27

Preparation of 2,2-Dimethoxy-1,7,7-trimethyl bicyclo-[2-2-1]heptane. Formula (IIa1)

To a flask with reflux condenser, (50 g) camphor and 100 ml methanol was taken. Subsequently, (76.2 g) (2.0 eq.) trimethyl orthoformate and several crystals of p-toluenesulfonic acid were added into the reaction mixture. The mixture was heated to reflux temperature (65-68° C.) for 24 hrs. After completion of the reaction, reaction mass was cooled at 25-30° C. and dichloromethane and water was added. The reaction mixture was stirred for 10 min. and the layer was separated, the organic layers was washed with water and brine and concentrate it on rotavapor, yellow color liquid product was obtained.

Weight of 2,2-dimethoxy camphor=55.5 g (% yield 85.3%)
ESI-MS (+ve mode)=166.8 (M-OMe)$^+$.
GC purity=65.44%

EXAMPLE-28

Preparation of 1,5',7,7-tetramethylspiro[bicyclo[2.2.1]heptane-2,2'-[1,3]dioxane]-5'-carboxylic acid. Formula (IIb1)

In a 500 ml three neck round bottom flask, (24.21 g) 2,2-bis(hydroxymethyl)propionic acid and 150 ml toluene was taken and subsequently several crystals of p-toluenesulfonic acid was added. The mixture was heated to reflux (110-115° C.), (55 g) 2,2-dimethoxy-1,7,7-trimethyl bicyclo-[2-2-1]heptane [Ha1] in 50 ml toluene was added dropwise. The mixture was heated to reflux (110-115° C.) for 6 hours, then the reaction mass was cooled at room temperature. It was concentrated on rotavapour, when thick slurry was obtained, water was added and extracted with ethyl acetate. Organic layer was washed with water and brine and concentrated on rotavapor. Subsequently, n-hexane was added and was stirred for 1 hr at room temperature, filtered, when white colored solid product was obtained.

Weight of above titled compound=20 g (% Yield=41.30%).
Melting point=175-180° C.
IR (in KBr): 3367-2638 cm$^{-1}$, 1703 cm$^{-1}$.
$^1$H NMR (400 MHz) CDCl$_3$: 4.13-4.01 (dd, J=11.6 and 2.8 Hz, 1H), 4.04-4.0 (dd, J=11.6 and 2.8 Hz, 1H), 3.69-3.62 (q, J=12.0 and 3.2 Hz, 2H), 2.11-2.06 (m, 1H), 1.94-1.89 (m, 1H), 1.82-1.80 (t, J=4.8 and 4.4 Hz, 1H), 1.71-1.70 (m, 1H), 1.54-1.51 (d, J=12.8 Hz, 1H), 1.32-1.25 (m, 1H), 1.14-1.10 (m, 1H), 1.01 (s, 3H), 0.92 (s, 3H), 0.86 (s, 3H).
ESI-MS=269.0 (M+1)$^+$.

EXAMPLE-29

Preparation of rapamycin-42-ester with 1,5',7,7-tetramethylspiro[bicyclo[2.2.1]heptane-2,2'-[1,3]dioxane]-5'-carboxylic acid. Formula (IId1)

In a 50 ml round bottom flask, (600 mg) 1,5'7,7-tetramethylspiro[bicyclo[2.2.1]heptane-2,2'-[1,3]dioxane]-5'-carboxylic acid [IIb1] and 16 ml dichloromethane were taken and cooled the reaction mass at 0-5° C. in ice bath. Subsequently, solution of (475 mg) triethyl amine in 0.5 ml dichloromethane was added dropwise, when clear solution was formed. (545.28 mg) 2,4,6-trichloro benzoyl chloride in 0.5 ml dichloromethane was added dropwise at 0-5° C. under nitrogen atmosphere and stirred the reaction mass at 0-5° C. to about 2 hrs. It was concentrated on rotavapour when oily product was obtained, toluene was added and stirred for 15 min and filtered.

In another 50 ml round bottom flask, filtrate i.e mixed anhydride 32 ml (2.236 mmole) was taken and the reaction mass was cooled to 5 to 10° C. (273.14 mg) (2.236 mmole) N,N-dimethyl amino pyridine (DMAP) and a solution of 1.362 g (1.491 m·moles) rapamycin in 15 ml toluene was added dropwise and stirred the reaction mass at 25-30° C. for 24 hrs. After completion of reaction, the reaction mass was diluted by adding toluene, filtered and washed the toluene layer with 10% sodium bicarbonate solution and then washed with water and brine solution. It was concentrated on rotavapour. White solid product was obtained.

Weight of 42-ester of rapamycin=1.9 g (Quantitative)
ESI-MS=1181.4 (M+NH$_3$)$^+$
(Above crude product is purified by column chromatography)

EXAMPLE-30

Preparation of CCI-779. Formula (I)

In 25 ml round bottom flask, (210 mg) rapamycin-42-ester, 1,5',7,7-tetramethylspiro[bicyclo[2.2.1]heptane-2,2'-[1,3]dioxane]-5'-carboxylic acid [IId1] and 5.5 ml THF was taken and the reaction mass was cooled at 0 to 5° C. Subsequently, 2N sulfuric acid (0.608 ml) was added dropwise in 15 min and stirred the reaction mass at 25-30° C. overnight. After completion of reaction the reaction mass was diluted by adding brine solution and extracted with diethyl ether. The ether layer was washed with 10% sodium bicarbonate solution and then with water and brine solution. It was concentrated on a rotavapour when oily product was obtained. This oily mass was stirred in cyclohexane, and the Cyclohexane was removed by filtration. The residue was concentrated till dryness to give white solid product. Crude CCI-779 was dissolved in acetone, and the acetone was then removed on rotavapour completely, and then was further dissolved in diethyl ether and precipitated by adding n-heptane dropwise to get white solid product. The product obtained was stirred at room temperature for about 2 hrs, filtered and washed the solid product with n-heptane.

Weight of CCI-779=110 mg (% Yield=59.25%)
HPLC purity=71.24%
ESI-MS=1047.6 (M+NH$_3$)$^+$
1052.3 (M+Na)$^+$

EXAMPLE-31

Preparation of 9,9-dimethoxy-9H-fluorene. Formula (IIa2)

To a flask with reflux condenser, (2.5 g) 9-fluorenone and 5 ml methanol was taken. Subsequently, (2.5 g) (1.7 eq.) trimethyl orthoformate and 2 drops (catalytic amount) of hexafluorophosphoric acid was added. The mixture was heated at reflux temperature (65-67° C.) for 20 hrs. Then the reaction mixture was cooled at 25-30° C., subsequently dilute solution of sodium bicarbonate was added and extracted by ethyl acetate. Organic layer was washed with water and brine and concentrated on rotavapor when yellow colored liquid product was obtained. Weight of 9,9-dimethoxy-9H-fluorene=2.93 g (% yield: 93.61%).
ESI-MS=194.8 (M-OMe)$^+$

EXAMPLE-32

Preparation of 5-methylspiro[[1,3]dioxane-2,9'-fluorene]-5-carboxylic acid. Formula (IIb2)

In a 100 ml three necked round bottom flask, (1.71 g) 2,2-bis(hydroxy methyl)propionic acid, 15 ml toluene and several crystals of p-toluenesulfonic acid was added. The mixture was heated to reflux (110-115° C.). Subsequently, (2.9 g) of 9,9-dimethoxy-9H-fluorene [IIa2] in 10 ml toluene was added. The mixture was heated to reflux (110-115° C.)

for 24 hours. Then the reaction mass was cooled to room temperature. It was concentrated on rotavapour when thick slurry was obtained, water was added and extracted with ethyl acetate. The organic layer was washed with water and brine and concentrated on rotavapor and n-hexane was added and stirred for 1 hr at room temperature. The reaction mass was filtered when pale yellow colored solid product was obtained.

Weight of above titled compound=2.1 g (% Yield=55.7%).
Melting point=166-170° C.
HPLC purity=93.01%
IR (in KBr): 3367-2638 cm$^{-1}$, 1701 cm$^{-1}$.
$^1$H NMR (400 MHz) CDCl$_3$: 7.73-7.70 (m, 2H), 7.65-7.59 (t, J=7.72 and 8.8 Hz, 2H), 7.43-7.38 (q, J=7.6 Hz, 2H), 7.31-7.27 (m, 2H), 4.74-4.71 (d, J=12 Hz, 2H), 4.25-4.22 (d, J=12 Hz, 2H), 1.57 (s, 3H).
ESI-MS=296.8 (M+1)$^+$, 318.9 (M+Na)$^+$

EXAMPLE-33

Preparation of rapamycin-42-ester with 5-methyl-spiro[[1,3]dioxane-2,9'-fluorene]-5-carboxylic acid. Formula (IId2)

In 50 ml round bottom flask, was taken 100 mg 5-methylspiro[[1,3]dioxane-2,9'-fluorene]-5-carboxylic acid [IIb2], to it was added 5 ml dichloromethane when clear solution formed. Cool the reaction mass at 0-5° C. in ice bath. To it was added a solution of 68.28 mg triethyl amine in 0.3 ml dichloromethane dropwise under nitrogen atmosphere. Added 82.3 mg 2,4,6-trichloro benzoyl chloride in 0.5 ml dichloromethane dropwise at 0-5° C. The reaction mass was stirred at 0-5° C. for about 2 hr. It was concentrated on rotavapour when oily product obtained, to it was added 5 ml toluene, stirred for 10 min filtered and washed the residue with 5 ml toluene. The mother liquor was cooled to 0-5° C., added to it 41.22 mg N,N-Dimethyl amino pyridine (DMAP) in single lot. To it was added a solution of 77.06 mg rapamycin in 4 ml toluene dropwise. The reaction mass was stirred at 25-30° C. for 24 hrs. After completion of reaction the reaction mass filtered and washed the toluene layer with 10% sodium bicarbonate solution and then water and brine solution. It was concentrated on rotavapour when white solid product was obtained.

Weight of 42-ester of rapamycin=155 mg (Quantitative)
ESI-MS=1209.9 (M+NH$_3$)$^+$, 1230.4 (M+K)$^+$

EXAMPLE-34

Preparation of CCI-779. Formula (I)

In a 25 ml round bottom flask, (155 mg) rapamycin-42-ester with 5-methylspiro [[1,3]dioxane-2,9'-fluorene]-5-carboxylic acid [IId2] and 4 ml THF was taken and cooled the reaction mass at 0 to 5° C. Subsequently, 2N sulfuric acid (0.413 ml) was added dropwise in 15 minutes time interval. The reaction mass was stirred at 25-30° C. for about 40 hrs. After completion of reaction the reaction mass was diluted by adding brine and extracted with ethyl acetate. The organic layer was washed with 5% sodium bicarbonate solution then water and brine solution. Concentrate it on rotavapor when oily product was obtained. This oily mass was stirred in cyclohexane, and the cyclohexane was removed by filtration. The residue was concentrated till dryness to give white solid product.

Crude CCI-779 was dissolved in acetone, and the acetone was removed on rotavapour completely, and was further dissolved in diethyl ether and precipitated by adding n-heptane dropwise to get white solid product. The product obtained was stirred at room temperature for about 2 hrs, filtered and washed the solid product with n-heptane.

Weight of CCI-779=50 mg (% Yield=39.7%)
ESI-MS=1047.4 (M+NH$_3$)$^+$

EXAMPLE-35

Preparation of 1,1-Dimethoxy cyclooctane. Formula (IIa7)

To a flask with reflux condenser, (5 g) cyclooctanone and 10 ml methanol was taken. Subsequently, (8.4 g) (2.0 eq.) trimethyl orthoformate and few crystals of p-toluenesulfonic acid were added. The mixture was stirred at 25-30° C. for about 2 hrs. The reaction mixture was cooled and reaction progress was monitored by TLC. Then remove the methanol on rotavapour and water was added and extracted with dichloromethane. Organic layer was washed with 5% sodium bicarbonate solution then water and brine solution. The reaction mixture was concentrated on rotavapor, when yellow colored oily product was obtained.

Weight of 1,1-dimethoxy cyclooctane=4 g (% yield 58.7%)

EXAMPLE-36

Preparation of 3-methyl-1,5-dioxaspiro[5.7]tridecane-3-carboxylic acid. Formula (IIb7)

In a 100 ml three necked round bottom flask, (3.11 g) 2,2-bis(hydroxy methyl) propionic acid, 30 ml toluene and few crystals of p-toluene sulfonic acid were taken. The mixture was heated to reflux (110-115° C.). To it was added dropwise 4.0 g 1,1-Dimethoxy-cyclooctane [IIa7] in 20 ml toluene. The mixture was heated to reflux (110-115° C.) for 3 hrs and then the reaction mass was cooled to 25-30° C. The reaction mass was filtered and filtrate was washed with water and brine solution. Organic layer was dried by adding sodium sulfate, concentrated on rotavapour, when thick brown color solid was obtained. Subsequently, n-hexane was added and stirred for 1 hr at room temperature, filtered, when white colored solid product was obtained.

Weight of above titled compound=1.65 g (% Yield=29.5%).
G.C. Purity=89.2%
Melting point=120-122° C.
IR (in KBr): 3369-2638 cm$^{-1}$, 1693 cm$^{-1}$.
$^1$H NMR (400 MHz) DMSO-D6: 12.42 (bs, 1H), 3.98-3.95 (d, J=11.6 Hz, 2H), 3.53-3.50 (d, J=11.6 Hz, 2H), 86-1.85 (d, J=6.0 Hz, 2H), 1.78-1.77 (d, J=6.0 Hz, 2H), 1.46 (s, 10H), 1.05 (s, 3H).
ESI-MS=242.9 (M+1)$^+$.

EXAMPLE-37

Preparation of rapamycin-42-ester with 3-methyl-1,5-dioxaspiro[5.7]tridecane-3-carboxylic acid. Formula (IId7)

In 50 ml round bottom flask, (300 mg) 3-methyl-1,5-dioxaspiro[5.7] tridecane-3-carboxylic acid [IIb7] and 8 ml dichloromethane was taken. The reaction mass was cooled to 0-5° C. in ice bath. Subsequently, solution of (250.87 mg) triethyl amine in 0.5 ml dichloromethane was added dropwise under nitrogen atmosphere. (302.2 mg) 2,4,6-trichloro benzoyl chloride in 0.5 ml dichloromethane was added dropwise at 0-5° C. and the reaction mass was stirred at 0-5° C. for about 2 hrs. The reaction mass was concentrated on rotavapour, when oily product was obtained. Toluene was added into the oily product and stirred for 10 min, filtered and the residue was washed with toluene. The mother liquor was cooled at 0-5° C. and subsequently, (151.36 mg) N,N-dimethyl amino pyridine (DMAP) was added in single lot. Solution of (566 mg) rapamycin in 10 ml toluene was added dropwise and the reaction mass was stirred at room temperature over night. After a completion of reaction, the reaction mass was filtered and the toluene layer was washed with 5% sodium bicarbonate solution and then water and brine solution. The reaction mixture was concentrated on rotavapour when white solid product was obtained.

Weight of 42-ester of rapamycin=800 mg (Quantitative)
ESI-MS=1155.6 $(M+NH_3)^+$.
HPLC purity=74.22%

EXAMPLE-38

Preparation of CCI-779. Formula (I)

In a 25 ml round bottom flask, (155 mg) rapamycin-42-ester with 3-methyl-1,5-dioxaspiro[5.7]tridecane-3-carboxylic acid [IId7] and 20 ml THF was taken and the reaction mass was cooled at 0 to 5° C. Subsequently, 2N sulfuric acid (2.369 ml) was added dropwise in 15 minutes time interval. The reaction mass was stirred at 0-5° C. for about 3 hrs and then stirred at 25-30° C. for about 24 hrs. After completion of reaction, the reaction mass was diluted by adding brine and extracted with ethyl acetate, wash the organic layer with 5% sodium bicarbonate solution and then water and brine solution. The reaction mixture was concentrated on rotavapor when oily product was obtained. This oily mass was stirred in cyclohexane, and the cyclohexane was removed by filtration. The residue was concentrated till dryness to give white solid product.

Weight of CCI-779=700 mg (% Yield=99.57%)
ESI-MS=1047.4 $(M+NH_3)^+$

EXAMPLE-39

Preparation of 3-methyl-1,5-dioxaspiro[5.5]undecane-3-carboxylic acid. Formula (IIb5)

In a 100 ml three necked round bottom flask, (5.0 g) 2,2-bis(hydroxy methyl) propionic acid and 15 ml toluene was taken. Subsequently, (3.65 g) (1 eq.) cyclohexanone in 10 ml toluene and few crystals of p-toluene sulfonic acid was added. The mixture was heated to reflux (110-115° C.) for 3 hours. Then the reaction mass was cooled at 25-30° C. The reaction mass was filtered and filtrate was washed with water and brine solution. The organic layer was dried by adding sodium sulfate, concentrated on rotavapor when thick brown colored solid was obtained. To this solid n-hexane was added and stirred for 1 hr at room temperature, filtered, when white colored solid product was obtained.

Weight of above titled compound=3.2 g (% Yield=40.0%)
IR (in KBr): 3448.8 $cm^{-1}$, 1691.6 $cm^{-1}$.
$^1H$ NMR (400 MHz) $CDCl_3$: 4.18-4.15 (d, J=12 Hz, 2H), 3.71-168 (d, J=12 Hz, 2H), 1.83-1.80 (m, 2H), 1.72-1.69 (m, 2H), 1.57-1.49 (m, 4H), 1.43-1.38 (m, 2H), 1.20 (s, 3H).
ESI-MS=212.8 $(M-1)^+$. (−ve mode)

EXAMPLE-40

Preparation of Rapamycin-42-ester with 3-methyl-1,5-dioxaspiro[5.5]undecane-3-carboxylic acid. Formula (IId5)

In a 50 ml round bottom flask, (70 mg) 3-methyl-1,5-dioxaspiro[5.5]undecane-3-carboxylic acid [IIb5] and 2 ml dichloromethane was taken. The reaction mass was cooled at 0-5° C. in ice bath. (66.3 mg) triethyl amine in 0.1 ml dichloromethane was added drop wise under nitrogen atmosphere. (79.9 mg) 2,4,6-trichloro benzoyl chloride in 0.1 ml dichloromethane was added drop wise at 0-5° C. and the reaction mass was stirred at 0-5° C. for 2 hrs. It was concentrated on rotavapour, when oily product was obtained. To this oily product toluene was added and stirred for 10 min and filtered. The residue was washed with toluene, the mother liquor was cooled at 0-5° C. Subsequently, (40 mg) N,N-Dimethyl amino pyridine (DMAP) was added in single lot and solution of (100 mg) rapamycin in 4 ml toluene was added drop wise. The reaction mass was stirred at 25-30° C. for 24 hrs. After completion of reaction, the reaction mass was filtered and the toluene layer was washed with 5% sodium bicarbonate solution and then water and brine solution. It was concentrated on rotavapour when white solid product was obtained.

Weight of 42-ester of rapamycin=144 mg (Quantitative)
ESI-MS=1127.5 $(M+NH_3)^+$

EXAMPLE-41

Preparation of CCI-779. Formula (I)

In a 25 ml round bottom flask, (140 mg) Rapamycin-42-ester with 3-methyl-1,5-dioxaspiro[5.5]undecane-3-carboxylic acid [IId5] and 2 ml THF was taken. The reaction mass was cooled to 0 to 5° C. 2N sulfuric acid (0.44 ml) was added drop wise in 15 minutes and the reaction mass was stirred at 0-5° C. for 3 hrs and again stirred at 25-30° C. for 24 hrs. After completion of reaction, the reaction mass was diluted by adding brine and extracted with ethyl acetate. The organic layer was washed with 5% sodium bicarbonate solution and then water and brine solution. It was concentrated on rotavapor, when oily product was obtained. This oily mass was stirred in cyclohexane, and the cyclohexane was removed by filtration. The residue was concentrated till dryness to give white solid product.

Weight of CCI-779=62 mg (% Yield=48.0%)
ESI-MS=1047.0 $(M+NH_3)^+$

EXAMPLE-42

Preparation of rapamycin-31-Trimethylsilyl-42-ester with 1,5',7,7-tetramethylspiro[bicyclo[2.2.1]heptane-2,2'-[1,3]dioxane]-5'-carboxylic acid. Formula (IId9)

In a 50-ml round bottom flask, (200 mg) 1,5',7,7-tetramethylspiro[bicyclo[2.2.1]heptane-2,2'-[1,3]dioxane]-5'-carboxylic acid [IIb1] and 6 ml dichloromethane was taken. The reaction mass was cooled to 0-5° C. in ice bath. Subsequently, a solution of (150.81 mg) triethyl amine in 0.5 ml dichloromethane was added drop wise under nitrogen atmosphere. (181.75 mg) 2,4,6-trichloro benzoyl chloride in 0.5 ml dichloromethane was added drop wise at 0-5° C. and the reaction to mass was stirred at 0-5° C. for about 2 hrs. It was concentrated on rotavapour when oily product was obtained. Subsequently, toluene was added and stirred for 10 min and filtered. The residue was washed with toluene. The mother liquor was cooled at 0-5° C. and (91.02 mg) N,N-dimethyl amino pyridine (DMAP) was added in single lot. Subsequently, a solution of (73 mg) 31-trimethylsilyl rapamycin in 3 ml toluene was added drop wise. The reaction mass was stirred at room temperature over night. After completion of reaction, the reaction mass was filtered and the toluene layer was washed with 5% sodium bicarbonate solution then water and brine solution. The organic layer was dried by adding sodium sulfate. It was concentrated on rotavapor when white solid product was obtained.

Weight of 31-trimethylsilyl-42-ester of rapamycin=150 mg (Quantitative)

$$ESI\text{-}MS = 1253.3(M + NH_3)^+$$
$$= 1260.1(M + Na)^+$$

EXAMPLE-43

Preparation of CCI-779. Formula (I)

In a 25 ml round bottom flask, (91.52 mg) rapamycin-31-trimethylsilyl-42-ester with 1,5',7,7-tetramethylspiro[bicycle[2.2.1]heptane-2,2'-[1,3]dioxane]-5'-carboxylic acid [IId9] and 15 ml THF was taken and the reaction mass was cooled at 0 to 5° C. Subsequently, 2N sulfuric acid (0.073 ml) was added drop wise in 15 minutes time interval and the reaction mass was stirred at 25-30° C. for about 24 hrs. After completion of reaction, the reaction mass was diluted by adding brine solution and extracted with ethyl acetate. The organic layer was washed with 5% sodium bicarbonate solution and then water and brine solution. It was concentrated on rotavapor when oily product was obtained. This oily mass was stirred in cyclohexane, and the cyclohexane was removed by filtration. The residue was concentrated till dryness to give white solid product.

Weight of CCI-779=50 mg (% Yield=65.6%)
ESI-MS=1047.4 (M+NH$_3$)$^+$, 1054.01 (M+Na)$^+$

EXAMPLE-44

Preparation of rapamycin-31-acetate-42-ester with 1,5',7,7-tetramethylspiro[bicyclo[2.2.1]heptane-2,2'-[1,3]dioxane]-5'-carboxylic acid. Formula (IId8)

In a 50 ml round bottom flask, (500 mg) 1,5',7,7-tetramethylspiro[bicyclo[2.2.1]heptane-2,2'-[1,3]dioxane]-5'-carboxylic acid [IIb1] and 12 ml dichloromethane was taken. The reaction mass was cooled at 0-5° C. in ice bath. Subsequently, a solution of (395.8 mg) triethyl amine in 1 ml dichloromethane was added drop wise under nitrogen atmosphere. (454.4 mg) 2,4,6-trichloro benzoyl chloride in 1 ml dichloromethane was added drop wise at 0-5° C. The reaction mass was stirred at 0-5° C. for about 2 hrs. It was concentrated on rotavapour when oily product was obtained. This oily mass was stirred in toluene for 10 min and filtered. The residue was washed with toluene. The mother liquor was cooled at 0-5° C. and (227.6 mg) N,N-dimethyl amino pyridine (DMAP) was added in single lot. Solution of (170 mg) rapamycin-31-acetate in 2 ml toluene was added drop wise. The reaction mass was stirred at room temperature over night. After completion of reaction, the reaction mass as filtered and washed the toluene layer with 5% sodium bicarbonate solution and then water and brine solution. The organic layer was dried by adding sodium sulfate. It was concentrated on rotavapour when pale yellow colored solid product was obtained.

Weight of 31-Acetate-42-ester of rapamycin=214.5 mg (Quantitative)
Melting point: 65-71° C.
ESI-MS=939.45

EXAMPLE-45

Preparation of CCI-779. Formula (I)

In a 25 ml round bottom flask, (214.5 mg) rapamycin-31-acetate-42-ester with 1,5',7,7-tetramethylspiro[bicyclo[2.2.1]heptane-2,2'-[1,3]dioxane]-5'-carboxylic acid [IId8] and 15 ml THF was taken and the reaction mass was cooled at 0 to 5° C. Subsequently, 2N sulfuric acid (0.177 ml) was added drop wise in 15 minutes time interval and the reaction mass was stirred at 25-30° C. to about 24 hrs. After completion of reaction, the reaction mass was diluted by adding water and extracted with ethyl acetate. The organic layer was washed with 5% sodium bicarbonate solution then water and brine solution. It was concentrated on rotavapor, when oily product was obtained. This oily mass was stirred in n-hexane, and the n-hexane was removed by filtration. The residue was concentrated till dryness to give white solid product.

Weight of CCI-779=300 mg (% Yield=Quantitative)
ESI-MS=1048.2 (M+NH$_3$)$^+$

EXAMPLE-46

Preparation of rapamycin-42-ester with 1,5',7,7-tetramethylspiro[bicyclo[2.2.1]heptane-2,2'-[1,3]dioxane]-5'-carboxylic acid. Formula (IId1)

In a 50 ml round bottom flask, (50 mg) 1,5',7,7-tetramethylspiro[bicyclo[2.2.1]heptane-2,2'-[1,3]dioxane]-5'-carboxylic acid [IIb1] and 3 ml dichloromethane was taken and the reaction mass was cooled at 0-5° C. in ice bath. Subsequently, solution of (39.58 mg) triethyl amine in 0.2 ml dichloromethane was to added drop wise when clear solution formed. (45.44 mg) 2,4,6-trichloro benzoyl chloride in 0.2 ml dichloromethane was added drop wise at 0-5° C., under nitrogen atmosphere. The reaction mass was stirred at 0-5° C. for about 2 hrs. Concentrate it on rotavapour, when oily product was obtained. This oily mass was stirred in toluene for 15 min and filtered. The residue was washed with toluene.

In another 50 ml round bottom flask, filtrate i.e mixed anhydride 10 ml (0.1863 m·mole) was taken and the reaction mass was cooled at 5 to 10° C. temperature. (22.76 mg) (0.1862 m·mole) N,N-dimethyl amino pyridine (DMAP) was added, when white suspension was formed. In another conical flask, (85.1 mg) (0.0931 m·mole) rapamycin in 4 ml toluene was taken and (19.96 mg) (0.1862 m·mole) 2,6-lutidine was added to formed clear solution This clear rapamycin containing solution was added dropwise into above white suspension. The reaction mass was stirred at 25-30° C. for 24 hrs. After completion of reaction, the reaction mass was diluted by adding toluene and filtered. The toluene layer was washed with 10% sodium bicarbonate solution and then washed with water and brine solution. It was concentrated on rotavapour, when white solid product was obtained.

Weight of 42-ester of rapamycin=123 mg (Quantitative)
ESI-MS=1181.6 (M+NH$_3$)$^+$

EXAMPLE-47

Preparation of CCI-779. Formula (I)

In a 25 ml round bottom flask, (123 mg) rapamycin-42-ester with 1,5',7,7-tetramethylspiro[bicyclo[2.2.1]heptane-2,2'-[1,3]dioxane]-5'-carboxylic acid [IId1] and 15 ml THF was taken and the reaction mass was cooled at 0 to 5° C. Subsequently, 2N sulfuric acid (0.4 ml) was added dropwise in 15 minutes time interval. The reaction mass was stirred at 25-30° C. overnight. After completion of reaction, the reaction mass was diluted by adding brine solution and extracted with diethyl ether. The ether layer was washed with 10% sodium bicarbonate solution then water and brine solution. It was concentrated on rotavapour, when oily product was obtained. This oily mass was stirred in n-hexane, and the n-hexane was removed by filtration. The residue was concentrated till dryness to give white solid product.

Weight of CCI-779=68 mg (% Yield=62.96%)
ESI-MS=1047.6 $(M+NH_3)^+$

EXAMPLE-48

Preparation of 1,5',7,7-tetramethylspiro[bicyclo[2.2.1]heptane-2,2'-[1,3]dioxane]-5'-carboxylic acid. [Formula (IIb1)]

In a 50 ml round bottom flask, 3 g 2,2-bis(hydroxymethyl) propionic acid, 10 ml toluene and several crystals of p-toluenesulfonic acid were taken. The mixture was heated to reflux (110-115° C.) and subsequently 5.06 g 2,2-diethoxy-1,7,7-trimethyl bicycle-[2-2-1]heptane in toluene was added dropwise. The mixture was further heated to reflux (110-115° C.) for 7 hours.

Then the reaction mass was cooled at room temperature, filtered and concentrated on rotavapour when oily product was obtained. Crude wt. 2.2 g.

Purification: Above crude product was purified by adding water and 10% sodium bicarbonate solution. Solid precipitate was obtained, which was filtered. The aqueous layer was acidified (at pH=4-5), white precipitate was obtained which was filtered.

Weight of above titled compound=1 g
(Melting point=172-175° C.).
IR (in KBr): 3367-2638 $cm^{-1}$, 1703 $cm^{-1}$.
$^1$H NMR (300 MZ) DMSO-D6: 12.45 (bs, 1H), 4.10-3.87 (m, 2H), 3.60-3.45 (m, 2H), 2.03-1.98 (bd, J=12.9 Hz, 1H), 1.91-1.82 (m, 1H), 1.74-1.71 (t, J=4.2 and 4.5 Hz, 1H), 1.65-1.58 (m, 1H), 1.49-1.45 (d, J=12.9 Hz, 1H), 1.32 (s, 1H), 1.24-1.14 (m, 1H) 1.10-1.0 (m, 1H), 0.89-0.84 (m, 3H), 0.83-0.68 (m, 9H).
ESI-MS=269.3 $(M+1)^+$

EXAMPLE-49

Preparation of 2,4,6-trichlorobenzoic-1,5',7,7-tetramethylspiro-bicyclo[2.2.1]heptane-2,2'-[1,3]dioxane]-5'-carboxylic anhydride. Formula (IIc1)

In a 50 ml round bottom flask, 50 mg 1,5',7,7-tetramethylspiro[bicyclo[2.2.1]heptane-2,2'-[1,3]dioxane]-5'-carboxylic and 3 ml acetone was taken. Subsequently, 53.9 mg potassium carbonate (anhydrous) was added in a single lot and the reaction mass was cooled at 0-5° C. in ice bath. Further 45.44 mg 2,4,6-trichloro benzoyl chloride in acetone was added dropwise at 0-5° C. into the reaction mixture and the reaction mass was stirred at 25-30° C. for about 3 hr. The reaction mass was filtered and concentrated on rotavapour to obtain oily product which is extracted with water and ethyl acetate. Layers are separated and the organic layer is concentrated to obtain white solid product.

Weight of above titled compound=90 mg
(Melting point=110-115° C.).
ESI-MS=367.22, 368.14
IR (in KBr): 1818.93 and 1793.86 $cm^{-1}$, 1734.06 $cm^{-1}$, 1577.82 $cm^{-1}$, 1215.19 $cm^{-1}$.

EXAMPLE-50

Preparation of 42-ester of Rapamycin with 1,5',7,7-tetramethylspiro[bicyclo[2.2.1]heptane-2,2'-[1,3]dioxane]-5'-carboxylic acid. [Formula to (IId)]

In a 50 ml round bottom flask, (90 mg) 2,4,6-trichlorobenzoic-1,5',7,7-tetramethylspiro-bicyclo[2.2:1]heptane-2,2'-[1,3]dioxane]-5'-carboxylic anhydride and 10 ml toluene was taken. The reaction mass was cooled at 5 to 10° C. temperature. Subsequently, (15 mg) N,N-dimethyl aminopyridine (DMAP) was added and after that solution of (25 mg) Rapamycin in toluene was added dropwise. The reaction mass was stirred at room temperature over night. After completion of reaction dilute the reaction mass by adding toluene and wash it with water and brine solution. Concentrate it on rotavapour. White solid product was obtained.

Weight of 42-ester of Rapamycin=60 mg (Quantitative)
ESI-MS=1187.18 $(M+Na)^+$
(Above product is identified by mass spectrum)

EXAMPLE 51

Preparation of CCI-779. Formula (I)

In 25 ml round bottom flask, (20 mg) 42-ester of Rapamycin (as obtained in Ex-9) and 5 ml THF was taken, the reaction mixture was cooled at 5 to 10° C. Subsequently, 2N sulfuric acid (0.15 ml) was added dropwise and reaction mixture was stirred at 25-30° C. overnight. After completion of reaction dilute the reaction mass by adding water and neutralize it by adding 10% sodium bicarbonate solution. The product was extracted with ethyl acetate and concentrated on rotavapour. Oily product was obtained.

Weight of CCI-779=10 mg
ESI-MS=1031 $(M+1)^+$

EXAMPLE-52

Preparation of rapamycin-31-Trimethylsilyl-42-ester with 1,5',7,7-tetramethylspiro[bicyclo[2.2.1]heptane-2,2'-[1,3]dioxane]-5'-carboxylic acid. [IId9]

In a 50 ml round bottom flask, (200 mg) 1,5',7,7-tetramethylspiro[bicyclo[2.2.1]heptane-2,2'-[1,3]dioxane]-5'-carboxylic acid [IIb1] and 6 ml dichloromethane was taken. The reaction mass was cooled to 0-5° C. in ice bath. Solution of (150.81 mg) triethyl amine in 0.5 ml dichloromethane was added drop wise under nitrogen atmosphere. (181.75 mg) 2,4,6-trichloro benzoyl chloride in 0.5 ml dichloromethane was added drop wise at 0-5° C. The reaction mass was stirred at 0-5° C. for about 2 hrs. Concentrate it on rotavapour when oily product was obtained. This oily mass was stirred in toluene for 10 min and filtered. The residue was washed with toluene. The mother liquor was cooled at 0-5° C. and (91.02 mg) N,N-dimethyl amino pyridine (DMAP) was added. Subsequently, a solution of (73 mg) 31-trimethylsilyl rapamycin in 3 ml toluene was added drop wise. The reaction mass was stirred at 25-30° C. to about 24 hrs. After completion of reaction, the reaction mass was filtered and washed the toluene layer with 5% sodium bicarbonate solution and then water and brine solution. The organic layer was dried by adding sodium sulfate. Concentrate it on rotavapor, white solid product was obtained.

Weight of 31-trimethylsilyl-42-ester of rapamycin=150 mg (Quantitative)

ESI-MS=1253.3 $(M+NH_3)^+$
1260.1 $(M+Na)^+$

EXAMPLE-53

Preparation of CCI-779. [I]

In a 25 ml round bottom flask, (91.52 mg) rapamycin-31-Trimethylsilyl-42-ester with 1,5',7,7-tetramethylspiro[bicyclo[2.2.1]heptane-2,2'-[1,3]dioxane]-5'-carboxylic acid [IId9] and 15 ml THF was taken and the reaction mass was cooled at 0 to 5° C. Subsequently, 2N sulfuric acid (0.073 ml) was added drop wise in 15 minutes time interval. The reaction mass was stirred at 25-30° C. for about 24 hrs. After completion of reaction, the reaction mass was diluted by adding brine solution and extracted with ethyl acetate. The organic layer was washed with 5% sodium bicarbonate solution and then water and brine solution. It was concentrated on rotavapor when oily product was obtained. This oily mass was stirred in cyclohexane, remove the cyclohexane by filtration. Concentrate the residue till dryness to give white solid product.

Weight of CCI-779=50 mg (% Yield=65.6%)
ESI-MS=1047.4 $(M+NH_3)^+$, 1052.01 $(M+Na)^+$

EXAMPLE-54

Preparation of rapamycin-31-trimethyl silyl-42-ester with 5-methyl-2,2-diphenyl-1,3-dioxane-5-carboxylic acid. [IId10]

In a flask, (163 mg) benzoic 5-methyl-2,2-diphenyl-1,3-dioxane-5-carboxylic anhydride (IIc3) was dissolved in 5.3 ml toluene. The reaction mass was cooled to 0-10° C., subsequently, (49.5 mg) N,N-dimethyl amino pyridine (DMAP) was added and stirred for 5 min. Then a solution of (100 mg) 31-trimethyl silyl rapamycin dissolved in 2 ml toluene was added and further stirred for 21 hr at 25-30° C. After completion of the reaction, water was added. Layers were separated, washed the toluene layer with 5% sodium bicarbonate solution and water. It was dried by adding sodium sulfate and concentrate it on rotavapour to obtain yellow colored oily compound.

Weight: 206 mg (Quantitative)

$$ESIMS = 1283.2[M + NH_3]^+ (+ve \text{ mode})$$
$$= 1264.5[M - 1]^+ (-ve \text{ mode})$$

EXAMPLE-55

Preparation of CCI-779. [I]

(189 mg) of 31-trimethyl silyl-42-ester of rapamycin with 5-methyl-2,2-diphenyl-1,3-dioxane-5-carboxylic acid [IId10] was dissolved in 2.8 ml THF and cooled to 0-5° C. Into the reaction mass 0.52 ml 2N sulphuric acid was added and stirred at 25-30° C. for 24 hrs. Then 2 ml THF and 0.52 ml 2 N sulphuric acid was added and stirred at 25-30° C. for 76 hrs. It was then concentrated on rotavapour, residue was dissolved in 2 ml ethyl acetate, and 2-3 drop perchloric acid $(HClO_4)$ diluted with 1 ml water was added. The reaction mixture was stirred at 25-30° C. for 24 hrs and reaction mass was dumped into water, and extracted with ethyl acetate. The layers were separated and washed the organic layer with 10% sodium bicarbonate solution and then water. It was dried over sodium sulfate, concentrated on rotavapor to obtain yellow colored oily compound.

Weight: 143 mg $$ESI\text{-}MS = 1031.3[M + 1]^+ (+ve \text{ mode})$$
$$= 1030.4[M^+] (-ve \text{ mode})$$

EXAMPLE-56

Preparation of 2,4,6-trichlorobenzoic 1,5',7,7-tetramethylspiro[bicyclo[2.2.1]heptane-2,2'-[1,3]dioxane]-5'-carboxylic anhydride. [IIc1]

In a 50 ml round bottom flask, (50 mg) 1,5',7,7-tetramethylspiro[bicyclo[2.2.1]heptane-2,2'-[1,3]dioxane]-5'-carboxylic acid [IIb1] and 3 ml acetone was taken, when a clear solution was formed. Subsequently, (53.9 mg) potassium carbonate was added and the reaction mass was cooled at 0-5° C. in ice bath. (45.44 mg) 2,4,6-trichloro benzoyl chloride in 0.5 ml acetone was added drop wise at 0-5° C. under nitrogen atmosphere. The reaction mass was stirred at 25-30° C. for about 3 hrs. After completion of the reaction water was added and it was extracted with ethyl acetate. The organic layer was concentrated on rotavapour, white solid product was obtained.

Weight of mixed anhydride=90 mg (% Yield=Quantitative)
HPLC purity=87.5%
IR (in KBr): 1818 $cm^{-1}$, 1734 $cm^{-1}$, 1215 $cm^{-1}$
$^1$H NMR (400 MHz) $CDCl_3$: 7.38 (s, 2H), 4.27-4.03 (m, 2H), 3.78-3.51 (m, 2H), 2.1-2.02 (m, 1H), 1.97-1.88 (m, 1H), 1.77-1.70 (m, 1H), 1.72-1.71 (m, 1H), 1.68-1.67 (m, 1H), 1.55-1.49 (m, 3H), 1.33-1.20 (m, 1H), 1.18-1.11 (m, 1H), 1.06-0.75 (m, 9H).

EXAMPLE-57

Preparation of rapamycin-42-ester with 1,5',7,7-tetramethylspiro[bicyclo[2.2.1]heptane-2,2'-[1,3]dioxane]-5'-carboxylic acid. [IId1]

In a 50 ml round bottom flask, (90 mg) 2,4,6-trichlorobenzoic 1,5',7,7-tetramethylspiro[bicyclo[2.2.1]heptane-2,2'-[1,3]dioxane]-5'-carboxylic anhydride [IIc1] was dissolved in 10 ml toluene. The reaction mass was cooled to 0 to 5° C. and subsequently, (15 mg) N,N-dimethyl amino pyridine (DMAP) was added, when white precipitate was formed. Solution of 25 mg rapamycin in 3 ml toluene was added drop wise and the reaction mass were stirred at 25-30° C. for 24 hrs. After completion of reaction the reaction mass was diluted by adding toluene, filtered and washed the toluene layer with 10% sodium bicarbonate solution and then washed with water and brine solution. It was concentrated on rotavapour, white solid product was obtained.

Weight of 42-ester of rapamycin=20 mg (% Yield=62.81%)
ESI-MS=1182.0 $(M+NH_3)^+$ 1187.1 $(M+Na)^+$

EXAMPLE-58

Preparation of CCI-779. [I]

In a 25 ml round bottom flask, (20 mg) rapamycin-42-ester with 1,5',7,7-tetramethylspiro[bicyclo[2.2.1]heptane-2,2'-[1,3]dioxane]-5'-carboxylic acid. [IId1] was dissolved in 3 ml THF and the reaction mass was cooled at 0 to 5° C. Subsequently, 2N sulfuric acid (0.15 ml) was added drop wise in 15 minutes time interval. The reaction mass was stirred at 25-30° C. for about 24 hrs. After completion of reaction dilute the reaction mass by adding brine solution and extract with ethyl acetate. The organic layer was washed with 10% sodium bicarbonate solution and then water and brine solution. It was concentrated on rotavapour, when oily product was obtained. This oily mass was stirred in cyclohexane, and the cyclohexane was removed by filtration. The residue was concentrated till dryness to give white solid product.

Weight of CCI-779=15 mg (% Yield=84.8%)

ESI-MS=1048.1 $(M+NH_3)^+$

While the invention has been described in terms of its specific embodiments, certain modifications and equivalents will be apparent to those skilled in the art and are intended to be included within the scope of the invention.

We claim:

1. A process for preparing a compound of Formula (I),

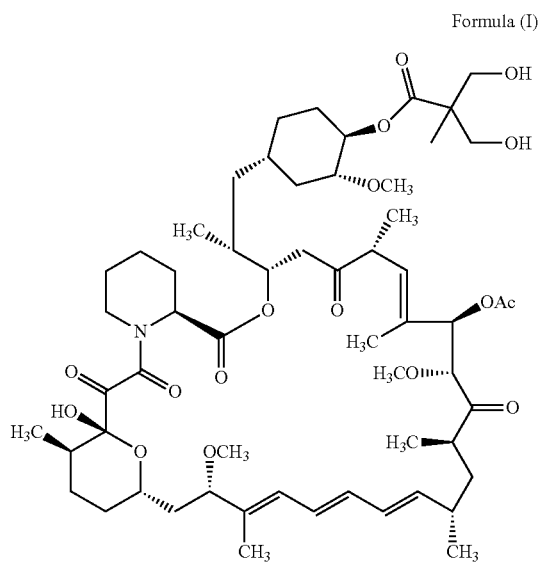 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](OC(=O)C(C)(CO)CO)[C@H](OC)C2)CC(=O)[C@H](C)/C=C(\C)[C@@H](OC(C)=O)[C@@H](OC)C(=O)[C@H](C)C[C@H](C)/C=C/C=C/C=C/1C]

Formula (I)

comprising:

(i) reacting 2,2-bis(hydroxymethyl)propionic acid of Formula (A),

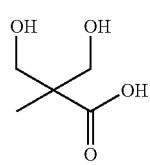

Formula (A)

with a suitable ketal of Formula (IIa)

$$R_1\underset{R_2}{\overset{OR}{\diagup}}OR$$

Formula (IIa)

in the presence of a suitable acid catalyst to obtain a compound of Formula (IIb),

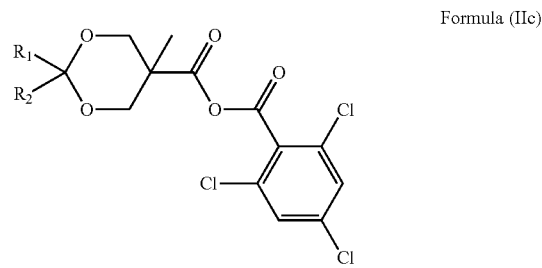

Formula (IIb)

wherein, each R is a $(C_1-C_3)$alkyl group; and each $R_1$ and $R_2$ independently represents a $(C_6-C_{10})$aryl group, or the $R_1$ and $R_2$ together with the carbon atom to which they are attached form a saturated or unsaturated fused or bridged $(C_6-C_{14})$ bicyclic or tricyclic ring structure which optionally may be substituted with at least one member selected from the group consisting of halogen, hydroxyl, $(C_1-C_4)$alkyl, $(C_1-C_4)$alkoxyl and halo$(C_1-C_4)$alkyl;

(ii) reacting the compound of Formula (IIb) obtained from step (i) with one or more suitable acylating agents in the presence of one or more suitable bases to form a mixed anhydride compound of Formula (IIc)

Formula (IIc)

wherein $R_1$ and $R_2$ are as defined above;

(iii) reacting the compound of Formula (IIc) obtained from step (ii) with rapamycin or 31-protected rapamycin in the presence of one or more suitable bases to give a suitably protected 42-ester rapamycin compound of Formula (IId)

Formula (IId)

wherein $R_1$ and $R_2$ are as defined above and P is either H or a suitable protecting group; and (iv) hydrolyzing the compound of Formula (IId) obtained from step (iii) with a suitable acid to obtain the compound of Formula (I).

2. The process of claim 1, wherein the suitable acid catalyst in step (i) is at least one member selected from the group consisting of organic acids and inorganic acids.

3. The process of claim 1, wherein the suitable acylating agent in step (ii) is at least one member selected from the group consisting of 2, 4, 6-trichloro benzoyl chloride, benzyl chloride, or suitable derivatives and mixtures thereof.

4. The process of claim 1, wherein the suitable base in step (ii) is a at least one member selected from the group consisting of triethyl amine, TMEDA, DMEDA, pyridine, alkali metal hydroxides, alkali alkaline earth metal carbonates, and mixtures thereof.

5. The process of claim 1, wherein the suitable base in step (iii) is a member selected from the group consisting of
an organic base selected from a member of the group consisting of trialkyl amines, TMEDA, DMEDA, pyridine, N-methyl imidazole, DMAP, or
an inorganic bases selected from a member of the group consisting of alkali metal hydroxides, alkali or alkaline earth metal carbonates, and
mixtures thereof.

6. The process of claim 1, wherein the suitable acid in step (iv) is at least one member selected from the group consisting of acetic acid, PTSA, PPTS and mixtures thereof.

7. The process of claim 1, wherein the suitable solvent in steps (i), (iii), or (iv) is a member selected from the group consisting of ethers, esters, hydrocarbons, halogenated hydrocarbons, DMF, DMSO, DMAc, NMP, acetonitrile, and mixtures thereof.

8. A compound of Formula (IIb):

Formula (IIb)

wherein, each $R_1$ and $R_2$ independently represents a ($C_6$-$C_{10}$)aryl group; or $R_1$ and $R_2$ together with the carbon atom to which they are attached form a saturated or unsaturated fused or bridged ($C_6$-$C_{14}$)bicyclic or tricyclic ring structure which optionally may be substituted with at least one member selected from the group consisting of halogen, hydroxyl, ($C_1$-$C_4$)alkyl, ($C_1$-$C_4$) alkoxyl, and halo($C_1$-$C_4$)alkyl.

9. The compound of claim 8 which is selected from a member of the group consisting of IIb1

IIb2

IIb3

10. A compound of Formula (IIc):

Formula (IIc)

wherein, each $R_1$ and $R_2$ independently represents a ($C_6$-$C_{10}$)aryl group, or $R_1$ and $R_2$ together with the carbon atom to which they are attached form a saturated or unsaturated fused or bridged ($C_6$-$C_{14}$) bicyclic or tricyclic ring structure which optionally may be substituted with at least one member selected from the group consisting of halogen, hydroxyl, ($C_1$-$C_4$)alkyl, ($C_1$-$C_4$) alkoxyl, and halo($C_1$-$C_4$)alkyl.

11. The compound of claim 10 which is selected from a member of the group consisting of IIc1

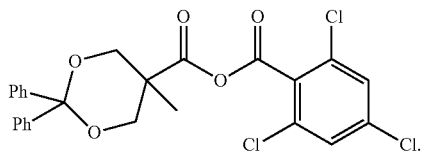

12. A compound of Formula (IId):

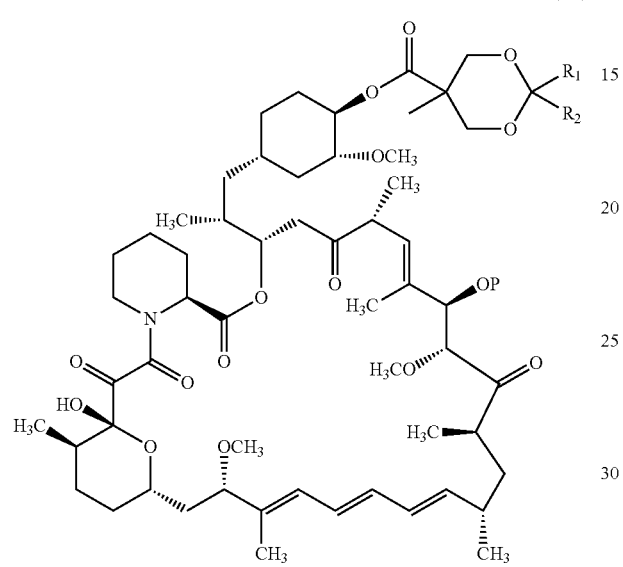

wherein each $R_1$ and $R_2$ independently represents a $(C_6$-$C_{10})$aryl group, or $R_1$ and $R_2$ together with the carbon atom to which they are attached form a saturated or unsaturated fused or bridged $(C_6$-$C_{14})$ bicyclic or tricyclic ring structure which optionally may be substituted with at least one member selected from the group consisting of halogen, hydroxyl, $(C_1$-$C_4)$alkyl, $(C_1$-$C_4)$ alkoxyl, or halo$(C_1$-$C_4)$alkyl.

13. The compound of claim 12 which is selected from a member of the group consisting of

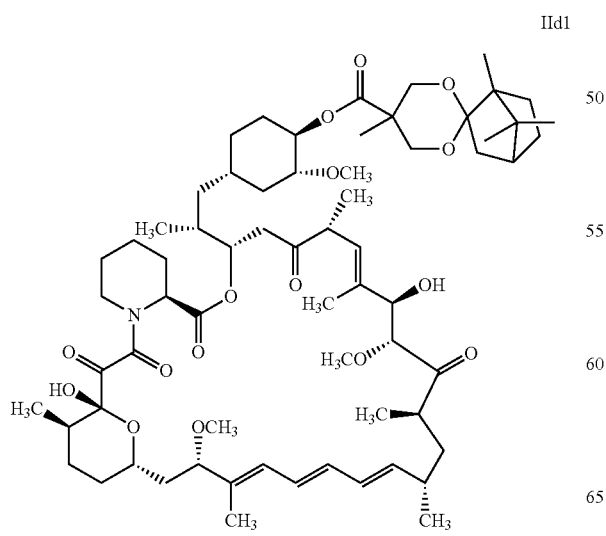

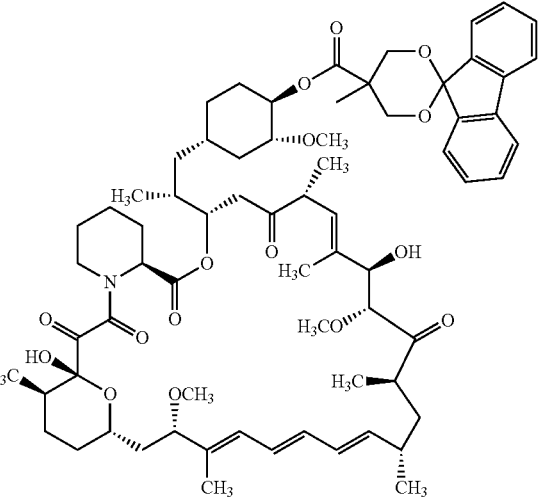

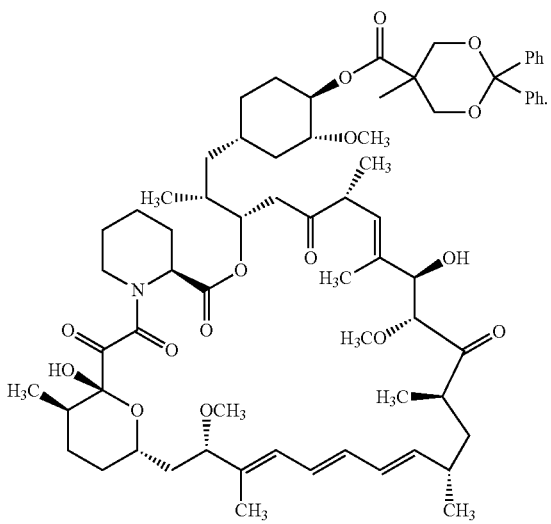

14. A process for preparing CCI-779 of Formula (I),

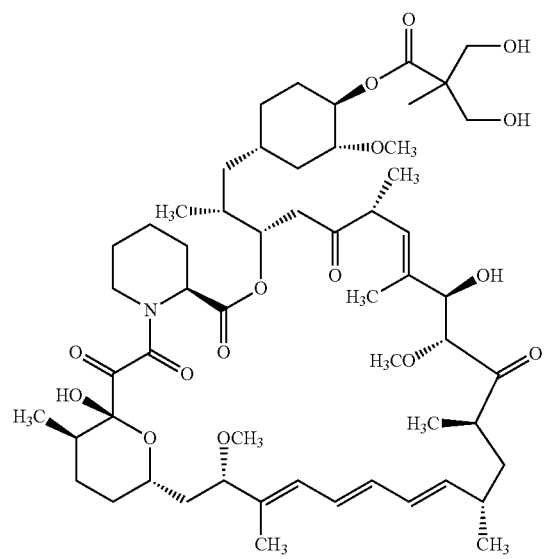

comprising:
(i) reacting rapamycin of Formula (R),

Formula (R)

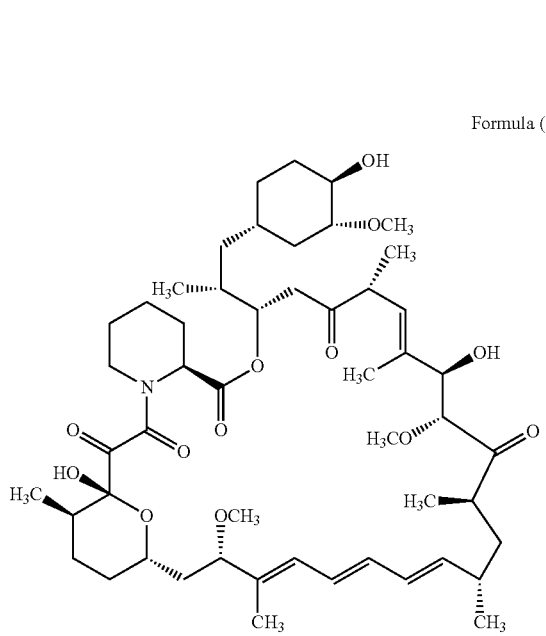

with one or more suitable acylating agents in the presence of one or more suitable bases to give a compound of Formula (Ia);

Formula (Ia)

Formula (Ia)
(ii) converting the compound of Formula (Ia) obtained from step (i) to 31-monoacetate of Formula (Ib) with one or more suitable bases in the presence of one or more suitable solvents;

Formula (Ib)

(iii) selectively esterifying the compound of Formula (Ib) obtained from step (ii) at the 42-position with a suitable esterification reagent in the presence of one or more suitable solvents to obtain a compound of Formula (Ic); and Formula (Ic)

(iv) deprotecting 42-ester and 31-acetyl group of the compound of Formula (Ic) obtained from step (iii) with one or more suitable acids in the presence of one or more suitable solvents to give the CCI-779 of Formula (I).

15. The process of claim 14, wherein the suitable acylating agent in step (i) is a member selected from the group consisting of
    alkanoyl ($C_2$-$C_{10}$) halides,
    benzoyl halides optionally substituted by a member selected from the group consisting of hydroxyl, halogen, ($C_1$-$C_4$)alkyl, ($C_1$-$C_4$)alkoxyl, or halo($C_1$-$C_4$)alkyl; and
    phenyl substituted alkanoyl halides wherein the alkanoyl portion has two to ten carbon atoms and the phenyl is unsubstituted or mono-or di-substituted with a member selected from the group consisting of halogen, hydroxyl, (C$_1$-C$_4$)alkyl, (C$_1$-C$_4$)alkoxyl, halo(C$_1$-C$_4$)alkyl, derivatives thereof and mixtures thereof.

16. The process of claim 14, wherein the suitable base in step (i) is at least one member selected from the group consisting of trialkyl amine, dialkyl amine, pyridine, DMAP and mixtures thereof.

17. The process of claim 14, wherein the suitable base in step (ii) is at least one member selected from the group consisting of alkali or alkaline earth metal carbonates, alkali or alkaline earth metal bicarbonates, alkali hydroxides, ammonia, ammonium carbonate, ammonium acetate, ammonium halide and mixtures thereof.

18. The process of claim 14, wherein the suitable solvent in step (ii) is at least one member selected from the group consisting of alcohols, esters, hydrocarbons, halogenated hydrocarbons, DMF, DMSO, DMAc, NMP, acetonitrile and mixtures thereof.

19. The process of claim 14, wherein the suitable esterification reagent in step (iii) is at least one member selected from the group consisting of 2,4,6-trichlorobenzoic 2,2,5-trimethyl-1,3-dioxane-5-carboxylic anhydride, methyl 2,2,3,3,6,9,9,10,10-nonamethyl-4,8-dioxa-3,9-disilaundecane-6-carboxylate, or suitable derivatives, and mixtures thereof.

20. The process of claim 14, wherein the suitable solvent in step (iii) is at least one member selected from the group consisting of esters, hydrocarbons, halogenated hydrocarbons, DMF, DMSO, DMAc, NMP, acetonitrile, and mixtures thereof.

21. The process of claim 14, wherein the suitable acid in step (iv) is at least one member selected from the group consisting of sulphuric acid, hydrochloric acid, phosphoric acid, acetic acid, PTSA, PPTS, and mixtures thereof.

22. The process of claim 14, wherein the suitable solvent in step (iv) is at least one member selected from the group consisting of ethers, esters, hydrocarbons, halogenated hydrocarbons, DMF, DMSO, DMAc, NMP, acetonitrile or mixtures thereof.

23. A process for preparing a compound of Formula (Ia),

Formula (Ia)

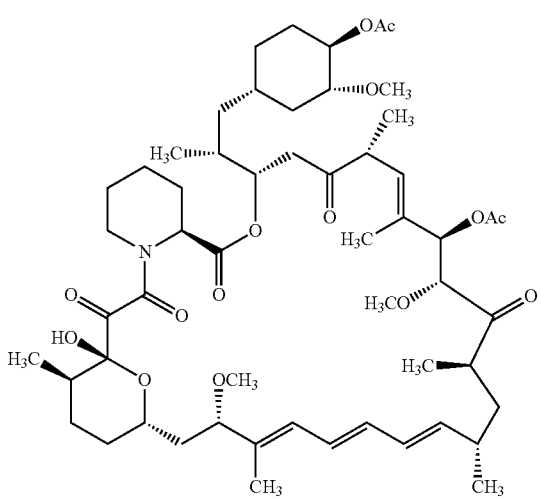

comprising:
reacting rapamycin of Formula (R),

Formula (R)

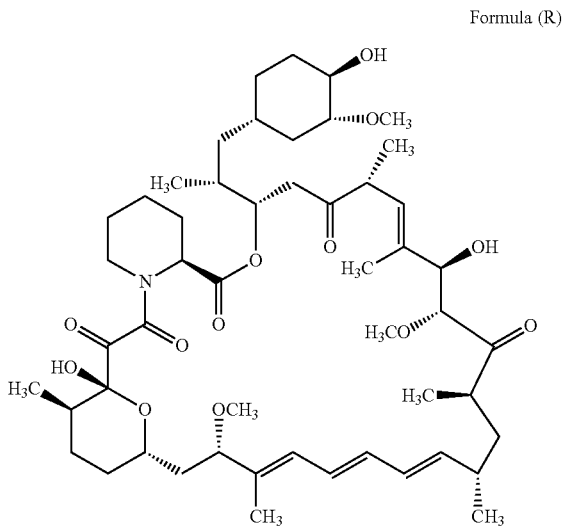 [SMILES: CO[C@H]1C[C@@H]2CC[C@@H](C)[C@@](O)(O2)C(=O)C(=O)N2CCCC[C@H]2C(=O)O[C@H]([C@H](C)C[C@@H]2CC[C@@H](O)[C@H](OC)C2)CC(=O)[C@H](C)/C=C(\C)[C@@H](O)[C@@H](OC)C(=O)[C@H](C)C[C@H](C)/C=C/C=C/C=C/1C]

with one or more suitable acylating agents in the presence of one or more suitable bases to give a compound of Formula (Ia)

Formula (Ia)

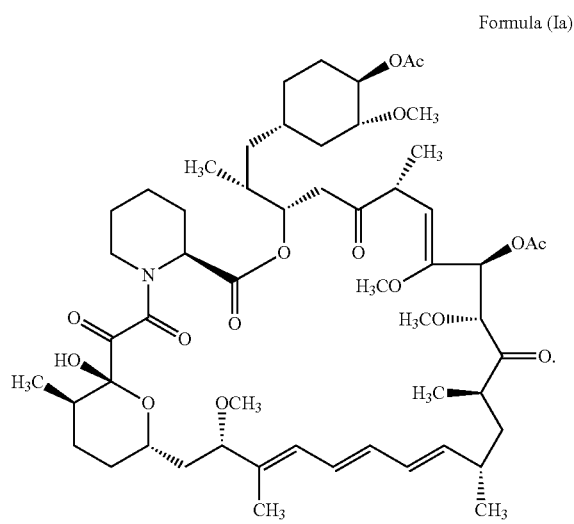 [SMILES: CO/C1=C\[C@@H](C)C(=O)C[C@@H]([C@H](C)C[C@@H]2CC[C@@H](OC(C)=O)[C@H](OC)C2)OC(=O)[C@@H]2CCCCN2C(=O)C(=O)[C@]2(O)O[C@@H](CC[C@H]2C)C[C@H](OC)/C(C)=C/C=C/C=C/[C@@H](C)C[C@@H](C)C(=O)[C@H](OC)[C@@H]1OC(C)=O]

24. The process of claim 23, wherein the suitable acylating agent is a member selected from the group consisting of
alkanoyl (C$_2$-C$_{10}$) halides,
benzoyl halides optionally substituted with a member selected from the group consisting of hydroxyl, halogen, (C$_1$-C$_4$)alkyl, (C$_1$-C$_4$)alkoxyl, or halo(C$_1$-C$_4$)alkyl; and
phenyl substituted alkanoyl halides, wherein the alkanoyl portion has two to ten carbon atoms and the phenyl is unsubstituted or mono- or di-substituted with a member selected from the group consisting of halogen, hydroxyl, (C$_1$-C$_4$)alkyl, (C$_1$-C$_4$)alkoxyl, halo(C$_1$-C$_4$)alkyl, derivatives thereof, and mixtures thereof.

25. The process of claim 23, wherein the suitable base is a member selected from the group consisting of trialkyl amine, dialkyl amine, pyridine, DMAP, and mixtures thereof.

* * * * *